United States Patent
Wei et al.

(10) Patent No.: US 8,658,837 B2
(45) Date of Patent: Feb. 25, 2014

(54) INTERMEDIATES FOR THE SYNTHESIS OF BENZINDENE PROSTAGLANDINS AND PREPARATIONS THEREOF

(71) Applicants: Shih-Yi Wei, Yangmei (TW); Min-Kuan Hsu, Yangmei (TW); Ming-Kun Hsu, Yangmei (TW)

(72) Inventors: Shih-Yi Wei, Yangmei (TW); Min-Kuan Hsu, Yangmei (TW); Ming-Kun Hsu, Yangmei (TW)

(73) Assignee: Chirogate International Inc., Yangmei (TW)

( * ) Notice: Subject to any disclaimer, the term of this patent is extended or adjusted under 35 U.S.C. 154(b) by 0 days.

(21) Appl. No.: 13/954,191

(22) Filed: Jul. 30, 2013

(65) Prior Publication Data
US 2013/0317245 A1    Nov. 28, 2013

Related U.S. Application Data

(62) Division of application No. 13/216,378, filed on Aug. 24, 2011, now Pat. No. 8,524,939.

(51) Int. Cl.
C07C 39/12     (2006.01)
C07C 255/00    (2006.01)

(52) U.S. Cl.
USPC .................................... 568/733; 558/389

(58) Field of Classification Search
None
See application file for complete search history.

*Primary Examiner* — Andrew S Kosar
*Assistant Examiner* — John S Kenyon
(74) *Attorney, Agent, or Firm* — Ladas & Parry LLP

(57) ABSTRACT

Novel processes for preparing optically active cyclopentanones 1

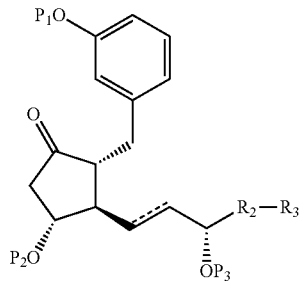

which are useful for the preparation of benzindene Prostaglandins and novel cyclopentanones are provided. The invention also provides novel processes of preparing benzindene Prostaglandins and novel intermediates for benzindene Prostaglandins.

5 Claims, No Drawings

INTERMEDIATES FOR THE SYNTHESIS OF BENZINDENE PROSTAGLANDINS AND PREPARATIONS THEREOF

CROSS REFERENCE APPLICATIONS

This application is a divisional of U.S. patent application Ser. No. 13/216,378 filed Aug. 24, 2011.

BACKGROUND OF THE INVENTION

1. Field of the Invention

The present invention relates to novel processes for preparing cyclopentanones of Formula 1,

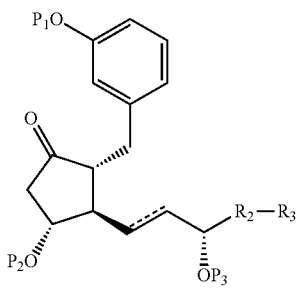

1 which are useful for the preparation of benzindene Prostaglandins. The invention also relates to novel cyclopentanones prepared from the processes.

2. Description of the Prior Art

Flolan (Epoprostenol) is the first drug approved by Food and Drug Administration for the treatment of pulmonary hypertension. However, Epoprostenol is extremely unstable and normally has a half-life of about 3~5 minutes and needs to be administered via continuous intravenous administration and be stored at lower temperatures. Benzindene Prostaglandins, such as UT15 (Treprostinil), are derivatives of Epoprostenol and are a new class of drugs for the treatment of pulmonary hypertension. Benzindene prostaglandins are more stable and thus more convenient and safer in utilization as compared to Epoprostenol.

As shown in Scheme 1, cyclopentanones of Formula 1a are important intermediates for the synthesis of benzindene prostaglandins, such as UT15 (Tetrahedron Letters (1982), 23(20), 2067-70):

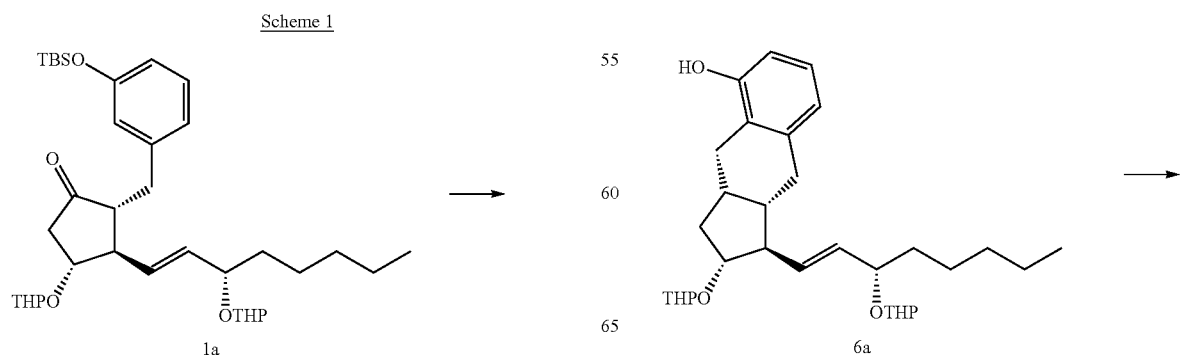

3
-continued

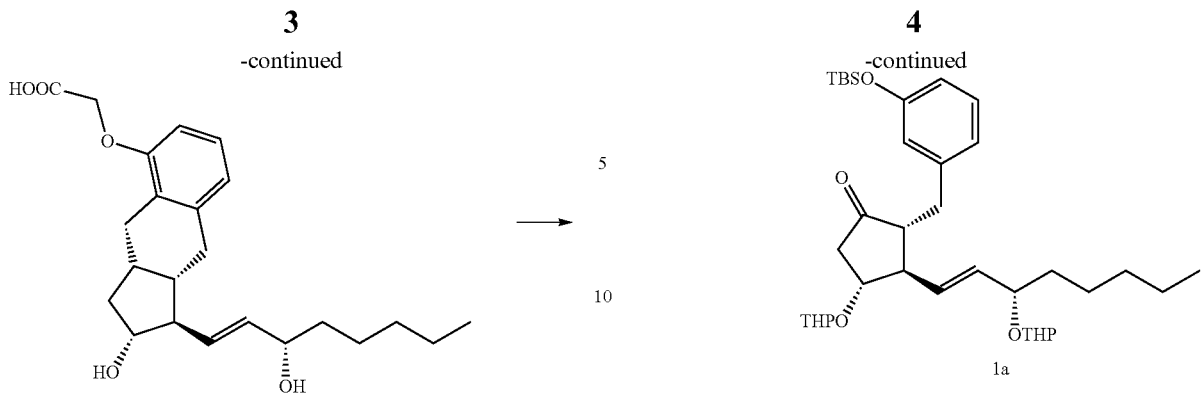

UT-15

However, as shown in Scheme 2, the synthesis of cyclopentanones of Formula 1a should be started with the intermediate B and undergoes eight steps (*J. Org. Chem.*, Vol. 43, No. 11, 1978), and would involve more than 20 chemical steps, including the steps for the synthesis of the intermediate B. Such synthesis is very complicated and only achieves a low yield.

Scheme 2

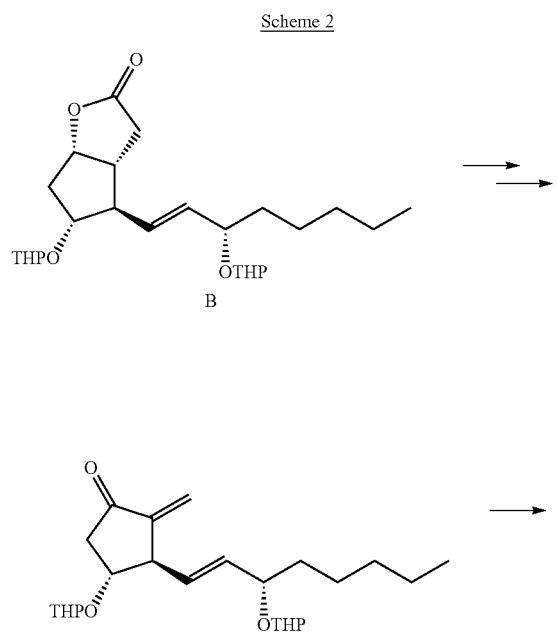

4
-continued

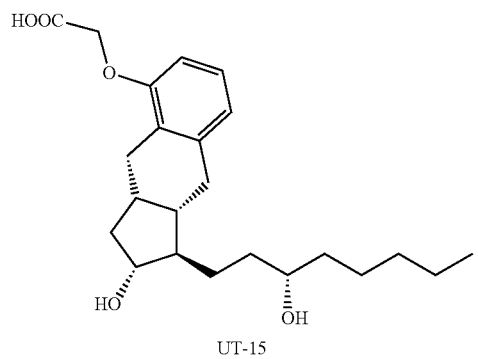

1a

Consequently, there is a demand in the industry for processes for the preparation of cyclopentanones of Formula 1 and benzindene prostaglandins that involve less steps and are more convenient to operate.

SUMMARY OF THE INVENTION

The present invention provides novel processes of preparing optically active cyclopentanones 1 and novel cyclopentanones.

The invention also provides novel processes of preparing benzindene Prostaglandins and novel intermediates for benzindene Prostaglandins.

DETAILED DESCRIPTION OF THE INVENTION

I. Definition

The term "alkyl" used herein refers to a straight or branched hydrocarbon group containing 1 to 30 carbon atoms, such as methyl, ethyl, isopropyl, tert-butyl, and the like; or a cyclic saturated hydrocarbon group having 3 to 10 carbon atoms, such as cyclopropyl, cyclopentyl, cyclohexyl, menthyl, and the like.

The term "lower alkyl" used herein refers to a straight or branched alkyl containing 1 to 6 carbon atoms such as methyl, ethyl, propyl, iso-propyl, n-butyl, tert-butyl, and the like.

The term "aryl" used herein refers to a a monocyclic or polycyclic aromatic hydrocarbon radical, such as phenyl, naphthyl, anthryl, phenanthryl and the like. The aryl may optionally be substituted with one or more substituents, including but not limited to, a halogen, an alkoxyl, a thioalkoxyl, an alkyl, and an aryl.

The term "aralkyl" used herein refers a straight or branched hydrocarbon containing 1 to 20 carbon atoms and one or more aryl group as described above, such as benzyl, benzhydryl, fluorenylmethyl, and the like.

Each of the above mentioned alkyl, aryl, and aralkyl may optionally be substituted with one or more substituents selected from the group consisting of halogen, alkyl, aryl, alkoxyl, aryloxy, thioalkoxyl, thioaryloxy, alkylamino, arylamino, cyano, nitro, alkoxycarbonyl, arylcarbonyl, arylaminocarbonyl, alkylaminocarbonyl, and carbonyl or a heterocyclic group selected from the group consisting of pyridinyl, thiophenyl, furanyl, imidazolyl, morpholinyl, oxazolinyl, piperidinyl, piperazinyl, tetrahydropyranyl, pyrrolidinyl, pyrrolidinonyl, and the like.

In the depiction of the compounds given throughout this description, a thickened taper line ( ) indicates a substituent which is in the beta-orientation (above the plane of the molecule or page), and a broken flare line ( ) indicates a substituent which is in the alpha-orientation (below the plane of the molecule or page).

II. Description of the Invention

A cyclopentanone of Formula 1

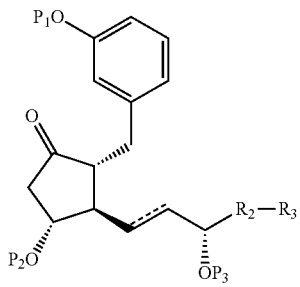

wherein $R_2$ is a single bond or a $C_{1-4}$-alkylene or a group of formula —$CH_2O$—; $R_3$ is a $C_{1-7}$-alkyl or an aryl or an aralkyl group, each of which is unsubstituted or substituted by a $C_{1-4}$-alkyl, a halogen, or a trihalomethyl; ═══ is a single or double bond; $P_1$ is a protecting group for the phenol group, which is preferably acid stable and includes, but is not limited to, unsubstituted alkyl, allyl, unsubstituted or substituted benzyl, acetyl, alkylcarbonyl, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, or $SiR_aR_bR_c$ wherein $R_a$, $R_b$ and $R_c$ are each independently a $C_{1-8}$ alkyl, phenyl, benzyl, a substituted phenyl, or a substituted benzyl, and more preferably $P_1$ is selected from allyl, unsubstituted or substituted benzyl, acetyl, alkylcarbonyl, and $SiR_aR_bR_c$ wherein $R_a$, $R_b$ and $R_c$ are each independently a $C_{1-8}$ alkyl, phenyl, benzyl, a substituted phenyl, or a substituted benzyl; $P_2$ and $P_3$ are the same or different and are protecting groups for the hydroxy group which are preferably base stable and include, but are not limited to, methoxymethyl methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, and $SiR_aR_bR_c$ wherein $R_a$, $R_b$ and $R_c$ are each independently a $C_{1-8}$ alkyl, phenyl, benzyl, a substituted phenyl, or a substituted benzyl, is prepared by a coupling reaction of an enantiomerically enriched ω-side chain unit of a cuprate derived from a halide of Formula II-1, a vinyl stannane of Formula II-2 or an alkyne of Formula II-3,

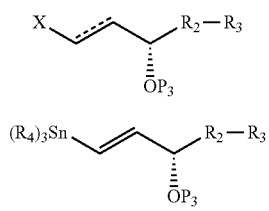

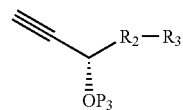

wherein X is a halogen; $R_4$ is a lower alkyl; and ═══, $R_2$, $R_3$, and $P_3$ are as defined above, as described in Chen, et. al., 1978, *J. Org. Chem.*, 43, 3450, U.S. Pat. No. 4,233,231, U.S. Pat. No. 4,415,501 and U.S. Pat. No. 6,294,679, which are all incorporated herein by reference, with an optically active cyclopentenone of Formula III,

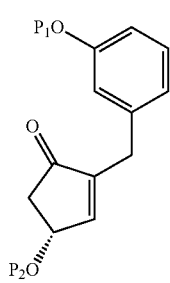

wherein $P_1$ and $P_2$ are as defined above, in a suitable solvent which can be tetrahydrofuran, 2-methyltetrahydrofuran, ethyl ether, isopropylether, methylbutylether, dimethoxyethane, toluene, heptane or hexane, or a mixture thereof, and preferably at a temperature ranging from −100° C. to 40° C.

The optically active cyclopentenone of Formula III can be prepared according to the process disclosed in the co-pending patent application filed on the even date and entitled "PROCESSES FOR PREPARING CYCLOPENTENONES AND NOVEL CYCLOPENTENONES FOR THE SYNTHESIS OF BENZINDENE PROSTAGLANDINS." Subsequently, the reaction is quenched with a base, e.g., ammonium hydroxide or the like, and subjected to a work-up procedure conducted in a conventional manner. The resultant crude product can be purified by a conventional method, such as column chromatography or recrystallization, or the unpurified product can be directly used in the next reaction. According to the present invention, the purification of the crude product 1 comprises deprotecting the $P_2$ and $P_3$ protecting groups of the resultant cyclopentanone 1, removing the impurities or isomers resulting from the coupling reaction by crystallization, and protecting again the hydroxy groups so as to obtain highly pure cyclopentanone of Formula 1.

As shown in Scheme 3, a compound of Formula 6 wherein $R_2$, $R_3$, ═══, $P_2$ and $P_3$ are as defined above is prepared from the cyclopentanone of Formula 1, Scheme 3

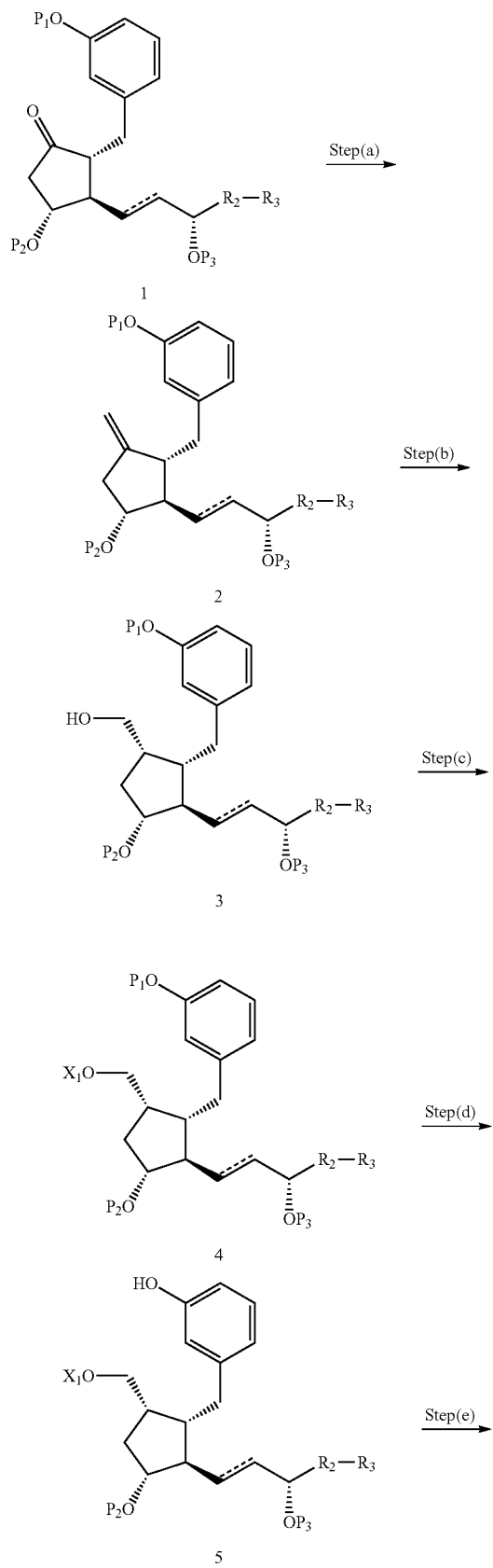

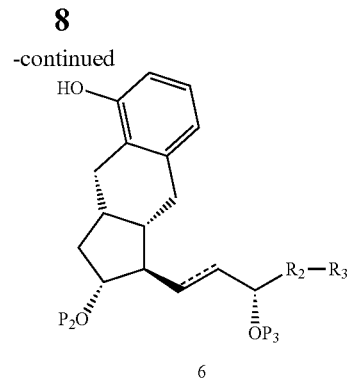

As shown in Step (a) of Scheme 3, the cyclopentanone of Formula 1 is subjected to a methylenelation with a Nozaki-Lombardo reagent (*Bull. Chem. Soc. Jpn.,* 53.1698 (1980)) which was prepared from dibromomethane, zinc, and titanium(IV) chloride, to form a compound of Formula 2. The reaction can be conducted in any suitable solvent, such as that selected from dichloromethane, tetrahydrofuran, ether, toluene, or hexane, or a mixture thereof. The reaction is carried out at a temperature ranging from −50° C. to 100° C., preferably from −20° C. to the room temperature. The Nozaki-Lombardo reagent is used in an amount such that the reactants are completely reacted as monitored by Thin Layer Chromatography (TLC). Upon completion of the reaction, the compound of Formula 2 can be isolated from the reaction mixture by a work-up procedure such as removing the excessive reagent, extraction, dehydration, concentration, and the like. The product may be further purified by column chromatography or by crystallization.

The methylene group can also be introduced by a two-step procedure as taught by Johnson in *J. Am. Chem. Soc.* 95, 6462 (1973), For example, the cyclopentanone of Formula 1 is reacted with an anion of methylphenyl-N-methyl-sulfoximine in a suitable solvent followed by treatment of the resulting crude adduct with aluminium amalgam in a solvent mixture of water-acetic acid-tetrahydrofuran so as to obtain a compound of Formula 2.

The compound of Formula 2 can be purified by removing the $P_2$ and $P_3$ protecting groups to obtain the corresponding, cyclopentanone of Formula 2 wherein $P_2$ and $P_3$ are replaced with H, purifying the corresponding cyclopentanone of Formula 2 by crystallization, with simultaneous removal of the impurities or isomers of Formula 2, and protecting again the hydroxy groups to obtain highly pure cyclopentanone of Formula 2 having the same or different protecting groups for the hydroxyl groups.

As shown in Step (b) of Scheme 3, the compound of Formula 2 is further converted into an alcohol compound of Formula 3. According to the present invention, the compound of Formula 2 is reacted with a boron reagent, such as 9-borabicyclo[3,3,1]nonane (9-BBN), followed by oxidation with basic hydrogen peroxide so as to give the alcohol compound of Formula 3.

As shown in Step (c) of Scheme 3, the alcohol compound of Formula 3 is further subjected to a sulfonylation reaction to obtain a compound of Formula 4 wherein $X_1$ is alkylsulfonyl, arylsulfonyl or aralkylsulfonyl, such as methanesulfonyl or p-toluenesulfonyl. The sulfonylation reaction is achieved in the presence of a base, such as an amine, e.g., triethylamine, by using an appropriate sulfonyl donor, such as methanesulfonyl chloride or p-toluenesulfonyl chloride.

As shown in Step (d) of Scheme 3, the compound of Formula 4 is subjected to a deprotection reaction so that $P_1$ is replaced with H or subjected to the deprotection reaction together with a hydrogenation of the double bond of the ω-side chain. The conditions suitable for the deprotection depend on the variable of $P_1$. When $P_1$ is a trialkylsilyl, the deprotection reaction is achieved using a fluoride ion, such as tetra-butylammonium fluoride. When $P_1$ is an unsubstituted or substituted benzyl, the deprotection reaction is achieved using a hydrogenation catalyst and a suitable base/electrophile reagent in a suitable solvent and in the presence of hydrogen. Suitable hydrogenation catalyst contains a metal selected from the group consisting of palladium, platinum, rhodium, and nickel and a mixture thereof. Examples of the catalyst include Pd—C, Pt—C, and Ni. Suitable solvent can be selected from tetrahydrofuran, ethyl acetate, methanol, ethanol, or toluene, or a mixture thereof. For the compound of Formula 4 where $P_1$ is an unsubstituted or substituted benzyl, and === is a double bond, the hydrogenation may be end with obtaining the compound of Formula 5 where === is a double bond, or may be continuously proceeded to obtain the compound of Formula 5 where === is a single bond, as monitored by HPLC or TLC.

As shown in Step (e) of Scheme 3, the compound of Formula 5 is further subjected to an intramolecular alkylation. The intramolecular alkylation is achieved using a suitable base in a suitable solvent. Suitable base can be selected from sodium hydride, potassium hydride, lithium hydride, potassium ter-butoxide or butyllithium, or a mixture thereof. Suitable solvent can be selected from tetrahydrofuran, 2-methyl tetrahydrofuran, glyme, or toluene, or a mixture thereof. The intramolecular alkylation will produce a minor amount of para-cyclized isomer of Formula IV.

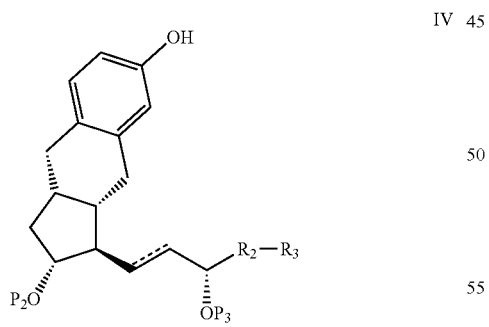

The para-cyclized isomer can be removed by column chromatography, or be removed in the subsequent crystallization step for obtaining crystalline intermediates for benzindene Prostaglandins.

According to an embodiment of the present invention, the invention provides a process for preparing a compound of Formula 6c

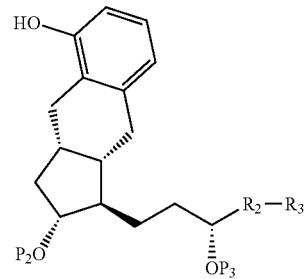

wherein $P_2$, $P_3$, $R_2$ and $R_3$ are as defined hereinbefore, comprising the steps of:

(1) reacting a compound of Formula III

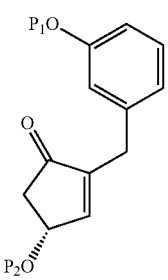

wherein $P_1$ and $P_2$ are as defined hereinbefore, with a cuprate derived from the compound of Formula II-1a, Formula II-2 or Formula II-3:

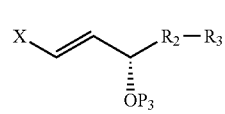

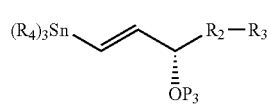

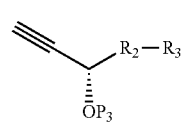

wherein X, $R_2$, $R_3$, $R_4$ and $P_3$ are as defined hereinbefore, to form a compound of Formula 1c

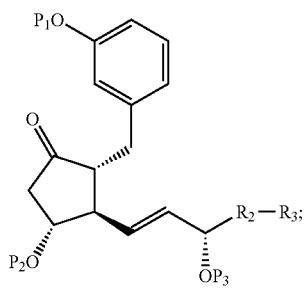

1c (2) methylenelation of the ketone radical of the compound of Formula 1c to form a methylene compound of Formula 2c

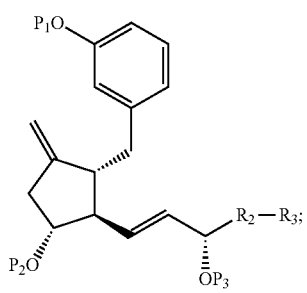

2c (3) hydroboration of the compound of Formula 2c with a boron reagent, such as 9-borabicyclo[3,3,1]nonane, followed by oxidation with basic hydrogen peroxide to give the alcohol compound of Formula 3c

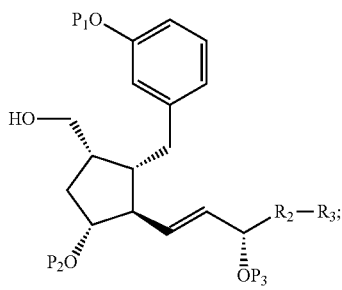

3c (4) sulfonylation of the compound of Formula 3c in the presence of a base with a sulfonyl donor, such as methanesulfonyl chloride or p-toluenesulfonyl chloride, to form a compound of Formula 4c

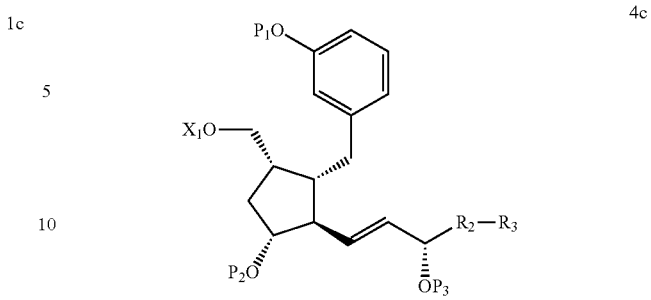

4c wherein $X_1$ is a sulfonyl group;

(5) removing the $P_1$ group and hydrogenating the double bound in ω-side chain to form a compound of Formula 5c

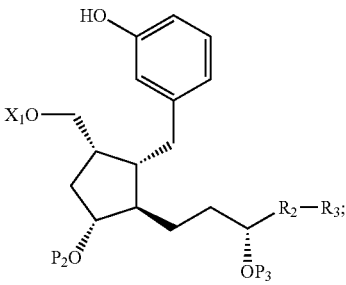

5c and (6) intramolecular alkylation of the compound of Formula 5c to form a compound of Formula 6c.

The methylenelation of step (2) may be conducted in the presence of a Nozaki-Lombardo reagent which was prepared from dibromomethane, Zinc, and Titanium(IV) chloride, or conducted by reacting the compound of Formula 1c with an anion of methylphenyl-N-methyl-sulfoximine in a suitable solvent followed by treating the resulting crude adduct with aluminum amalgam in a solvent mixture of water-acetic acid-tetrahydrofuran.

According to a preferred embodiment of the invention, in Formula 6c, $R_2$ is a single bond and $R_3$ is an amyl. $P_1$ is unsubstituted or substituted benzyl, $P_2$ and $P_3$ are independently protecting groups for the hydroxy group which are preferably selected from, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, and $SiR_aR_bR_c$ wherein $R_a$, $R_b$ and $R_c$ are each independently a $C_{1-8}$ alkyl.

As shown in Scheme 4. UT-15, can be easily prepared from the compound of Formula 6b, which corresponds to the compound of Formula 6 wherein ≡ is a single bond; $R_2$ is a single bond; $R_3$ is an amyl; $P_2$ and $P_3$ are protecting groups for hydroxy radicals.

Scheme 4

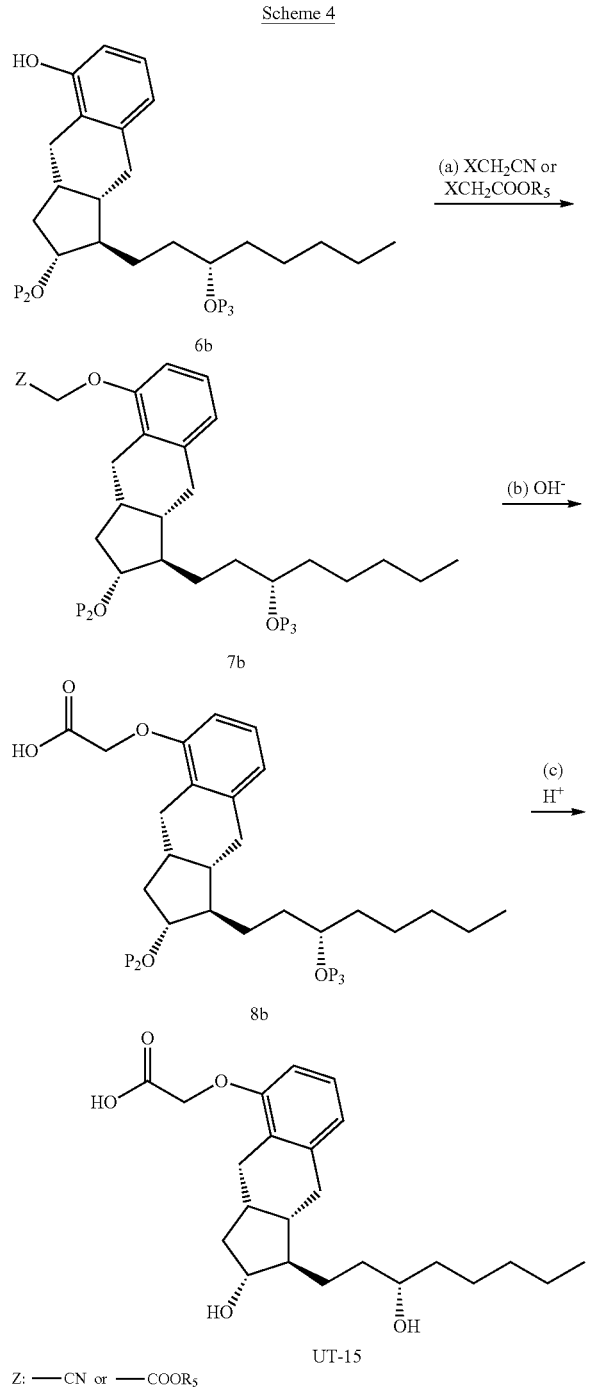

The process shown in Scheme 4 comprises:
(a) alkylating the phenol group of the compound of Formula 6b with an alkylating agent of XCH$_2$CN or XCH$_2$COOR$_5$, wherein X is a halogen such as Cl, Br, or I; R$_5$ is an alkyl;
(b) hydrolyzing the —CN or —COOR$_5$ radical with a base to form —COOH radical; and
(c) removing the protecting groups P$_2$ and P$_3$.

The above-mentioned steps for preparing UT-15 can be conducted in any order, such as in the order of (a)(b)(c), (a)(c)(b), or (c)(a)(b). Preferably, the process is conducted in the order of (c)(a)(b).

As shown in Scheme 5, UT-15 can also be prepared from the compound of Formula 6d, which corresponds to the compound of Formula 6 wherein === is a double bond; R$_2$ is a single bond; R$_3$ is an amyl; P$_1$ and P$_3$ are protecting groups for hydroxy radicals.

Scheme 5

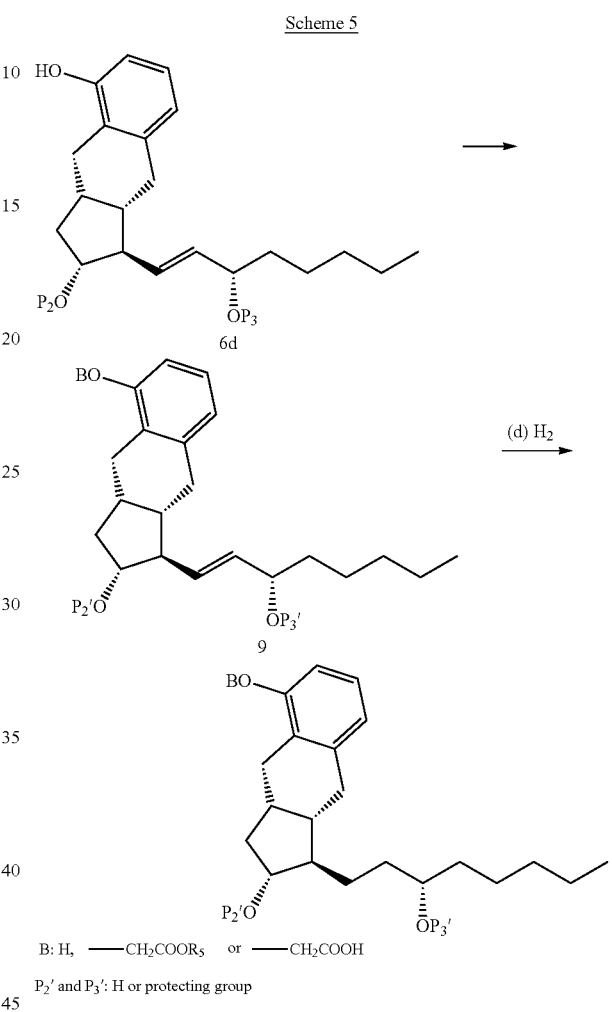

The process comprises, in addition to the above-mentioned steps (a), (b), and (c), (d) hydrogenating the double bond of the compound of Formula 6d, or the double bond of the compound of Formula 9 wherein B, P$_2$' and P$_3$' are H, or the double bond of the compound of Formula 9 wherein B is —CH$_2$COOR$_5$ and P$_2$' and P$_3$' are H or protecting group, or the double bond of the compound of Formula 9 wherein B is —CH$_2$COOH and P$_2$' and P$_3$' are H or protecting group, in the presence of a hydrogenation catalyst and a suitable base/electrophile reagent in a suitable solvent with hydrogen.

These steps can be conducted in any order, such as in the order of (a)(b)(c)(d), (a)(b)(d)(c), (d)(a)(b)(c), (a)(c)(b) (d), (a)(c)(d)(b), (a)(d)(c)(b), (d)(a)(c)(b), (c)(a)(b)(d), (c)(a)(d) (b), or (c)(d)(a)(b). For example, the compound of formula 6d can be first hydrogenated into the compound of formula 6b (i.e., undergoing step (d)), and then subjected to steps (a), (b), and (c) in any order. Preferably, the steps are conducted in the order of (c)(d)(a)(b), (a)(c)(b)(d) or (a)(b)(c)(d).

According to one embodiment, the present invention provides a process for preparing treprostinil (UT-15), comprising the steps of:

(1) reacting a compound of Formula IIIa

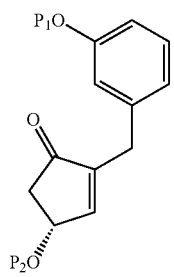

IIIa wherein $P_1$ is allyl, unsubstituted or substituted benzyl, acetyl, alkylcarbonyl, and $SiR_aR_bR_c$ wherein $R_a$, $R_b$ and $R_c$ are each independently a $C_{1-8}$ alkyl, phenyl, benzyl, a substituted phenyl, or a substituted benzyl; and $P_2$ is as defined hereinbefore, with a cuprate derived from the compound of Formula II-1a, Formula II-2 or Formula II-3:

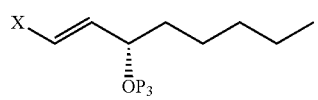

II-1a

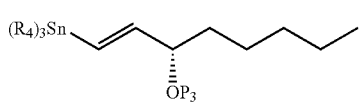

II-2

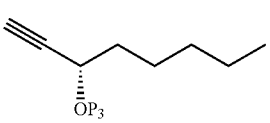

II-3 wherein X, $R_2$, $R_3$, $R_4$ and $P_3$ are as defined hereinbefore, to form a compound of Formula 1d

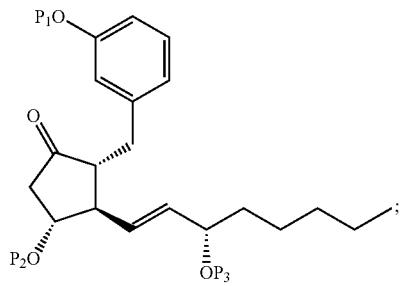

1d (2) methylenelation of the ketone radical of the compound of Formula 1d to for a methylene compound of Formula 2d

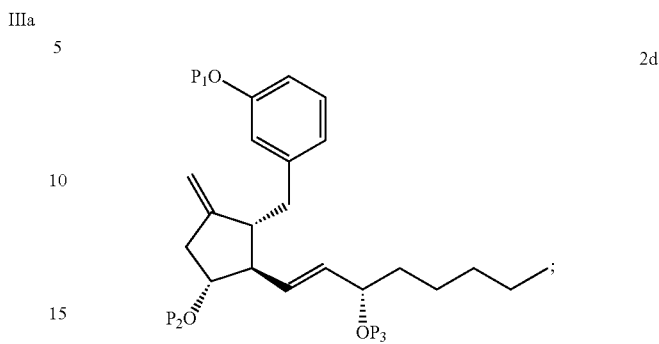

2d (3) hydroboration of the compound of Formula 2d with a boron reagent, such as 9-borabicyclo[3,3,1]nonane, followed by oxidation with basic hydrogen peroxide to give the alcohol compound of Formula 3d 3d (4) sulfonylation of the compound of Formula 3d in the presence of a base with a sulfonyl donor, such as methanesulfonyl chloride or p-toluenesulfonyl chloride, to form a compound of Formula 4d

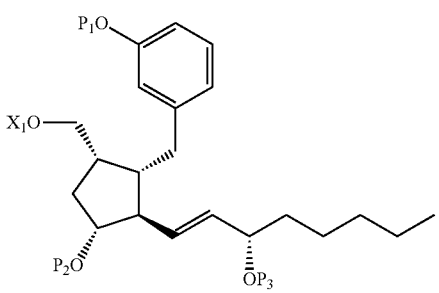

4d wherein $X_1$ is a sulfonyl group;

(5) removing the P₁ group to form a compound of Formula 5d,

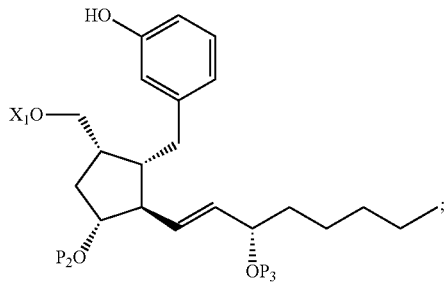

(6) intramolecular alkylation of the compound of Formula 5d to form a compound of Formula 6d

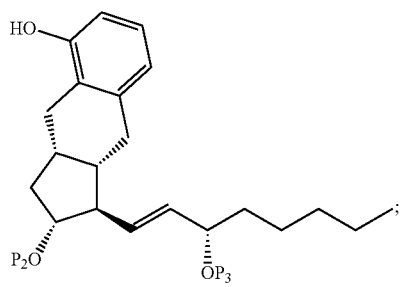

(7) removing the P₂ and P₃ groups to form a compound of Formula 7d

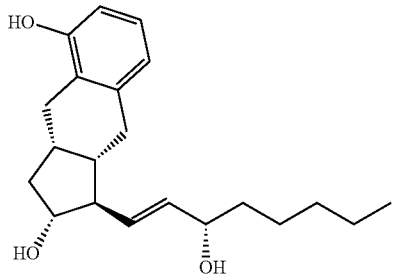

(8) hydrogenating the double bound in the ω-side chain of the compound of Formula 7d to form a compound of Formula 8d

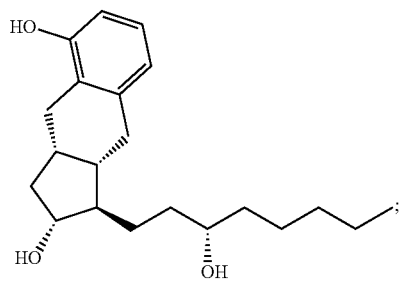

(9) alkylating the phenol group with an alkylating agent of XCH₂CN or XCH₂COOR₅ wherein X is halogen such as Cl, Br, or I; R₅ is an alkyl, to form a compound of Formula 9d

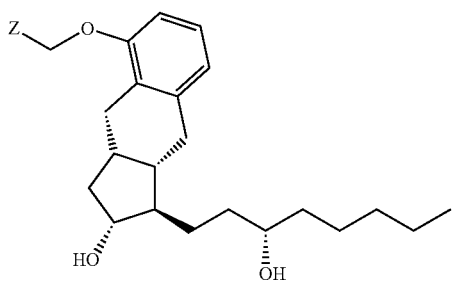

wherein Z is —CN or —COOR₅; and

(10) hydrolyzing the —CN or —COOR₅ radical of the compound of Formula 9d with a base to form treprostinil.

According to one embodiment, the present invention provides a process for preparing treprostinil (UT-15), comprising the steps of above mention (1)~(6), to form a compound of Formula 6d, and then

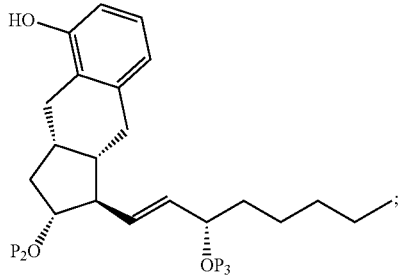

(7) alkylating the phenol group with an alkylating agent of XCH₂CN or XCH₂COOR wherein X is halogen such as Cl, Br, or I; R₅ is an alkyl, to form a compound of Formula 7D

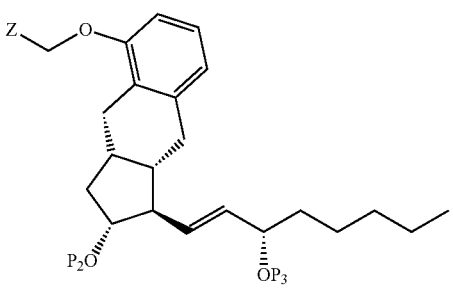

wherein Z is —CN or —COOR₅; and (8) removing the $P_2$ and $P_3$ groups to form a compound of Formula 8D

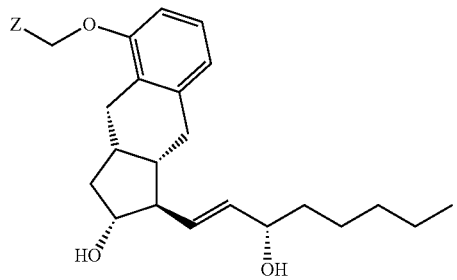

8D (9) hydrolyzing the —CN or —$COOR_5$ radical of the compound of Formula 8D with a base to form of Formula 9D

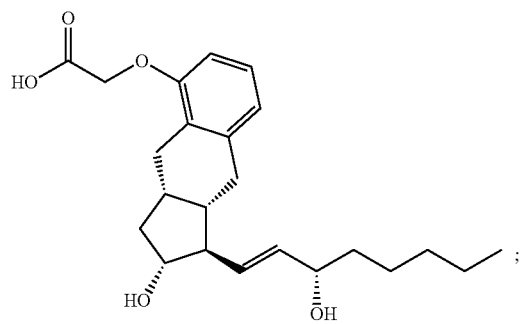

9D

(10) hydrogenating the double bound in the ω-side chain of the compound of Formula 9D to form treprostinil.

According to another embodiment, the present invention provides an alternative process for preparing treprostinil (UT-15), comprising the steps of:

(1) reacting a compound of Formula IIIa

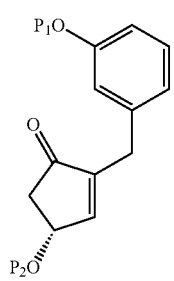

IIIa wherein $P_1$ is allyl, unsubstituted or substituted benzyl, acetyl, alkylcarbonyl, and $SiR_aR_bR_c$ wherein $R_a$, $R_b$ and $R_c$ are each independently a $C_{1-8}$ alkyl, phenyl, benzyl, a substituted phenyl, or a substituted benzyl; and $P_2$ is as defined hereinbefore, with a cuprate derived from the compound of Formula II-1b

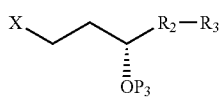

II-1b wherein X, $R_2$, $R_3$ and $P_3$ are as defined hereinbefore to form a compound of Formula 1b

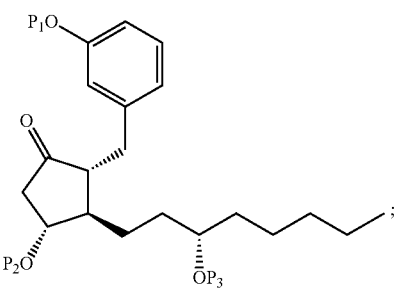

1b (2) methylenelation of the ketone radical of the compound of Formula 1b to form a methylene compound of Formula 2b

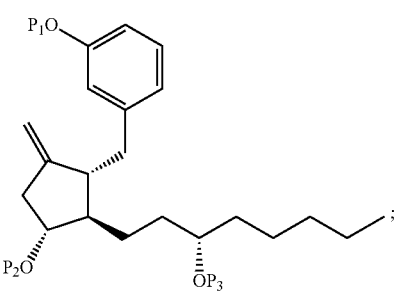

2b (3) hydroboration of the compound of Formula 2b with a boron reagent, such as 9-borabicyclo[3,3,1]nonane, followed by oxidation with basic hydrogen peroxide to give the alcohol compound of Formula 3b

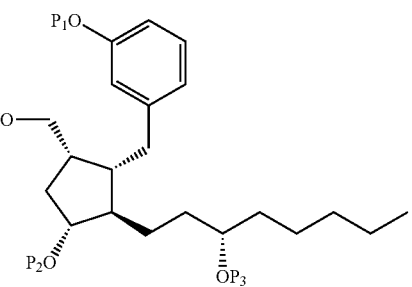

3b (4) sulfonylation of the compound of Formula 3b in the presence of a base with a sulfonyl donor, such as methanesulfonyl chloride or p-toluenesulfonyl chloride, to form a compound of Formula 4b

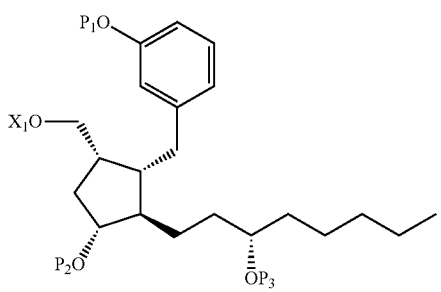

wherein $X_1$ is a sulfonyl group;

(5) removing the $P_1$ group to form a compound of Formula 5b,

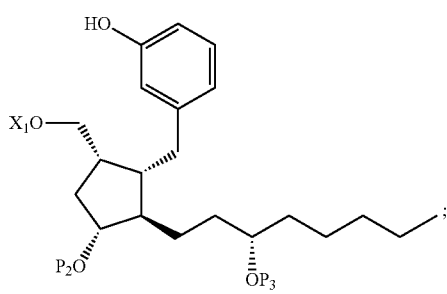

(6) intramolecular alkylation of the compound of Formula 5b to form a compound of Formula 6b

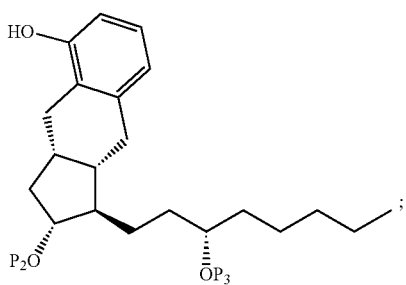

(7) removing the $P_2$ and $P_3$ groups to form a compound of Formula 8d

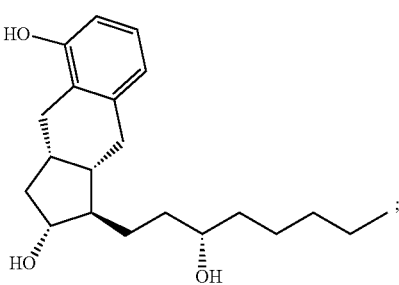

(8) alkylating of phenol group with an alkylating agent of $XCH_2CN$ or $XCH_2COOR_5$, wherein X is halogen such as Cl, Br, or I; $R_5$ is an alkyl to form a compound of Formula 9d

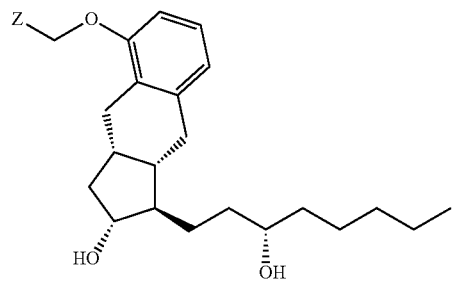

wherein Z is —CN or —$COOR_5$; and (9) hydrolyzing the —CN or —$COOR_5$ radical of the compound of Formula 9d with a base to form treprostinil.

According to another embodiment, the present invention provides an alternative process for preparing high-purity compound of Formula 8d

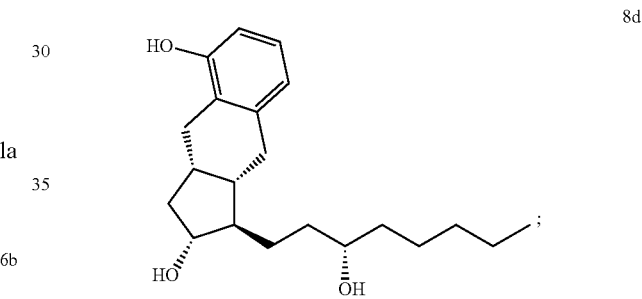

comprising the steps of:

(1) esterifying the compound of Formula 6d with an acyl donor such as acetic anhydride, acetyl chloride, benzoic anhydride, benzoyl chloride, or 4-biphenylcarbonyl chloride, in the presence of a base such as pyridine, triethylamine, sodium hydride, or potassium hydride, to form an ester compound of Formula 10d

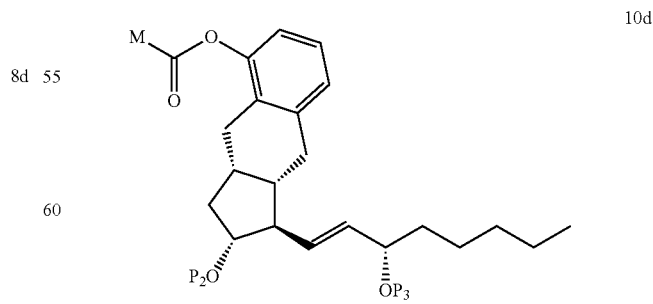

wherein M is a lower alkyl, or an unsubstituted or substituted phenyl; preferably, M is methyl, phenyl or 4-phenylphenyl;

(2) removing the P$_2$ and P$_3$ groups to form a crystalline compound of Formula 11d

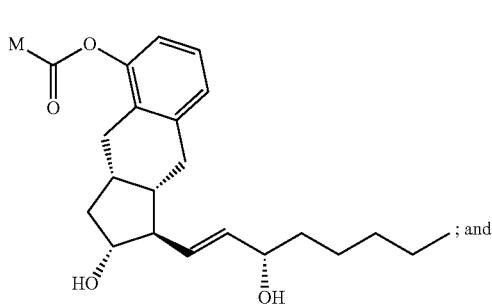

(3) hydrogenating the double bond in the ω-side chain of the compound of formula 11d and deacylating the hydrogenated compound; or first deacylating the compound of formula 11d and then hydrogenating the double bond in the ω-side chain of the deacylated compound to form a compound of Formula 8d.

The present invention also pertains to a novel compound of Formula 1d

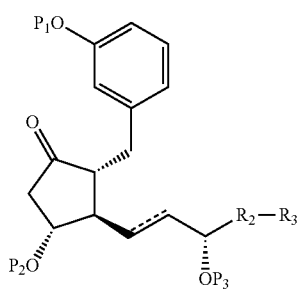

wherein ═══ is single bond or double bond; R$_2$ is a single bond or a C$_{1-4}$-alkylene or a group of formula —CH$_2$O—; R$_3$ is a C$_{1-7}$-alkyl or an aryl or an aralkyl group, each of which is unsubstituted or substituted by a C$_{1-4}$-alkyl, a halogen, or a trihalomethyl; P$_1$ is an unsubstituted or substituted benzyl; P$_{2'}$ and P$_{3'}$ are respectively P$_2$ and P$_3$ as defined hereinbefore as protecting groups for the hydroxy radical or independently from each other H. When P$_{2'}$ and P$_{3'}$ are respectively P$_2$ and P$_3$, they are base stable, and can be independently selected from methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, and SiR$_a$R$_b$R$_c$ wherein R$_a$, R$_b$ and R$_c$ are each independently a C$_{1-8}$ alkyl, phenyl, benzyl, a substituted phenyl, or a substituted benzyl.

The present invention also pertains to a novel crystalline compound of Formula 8D-1

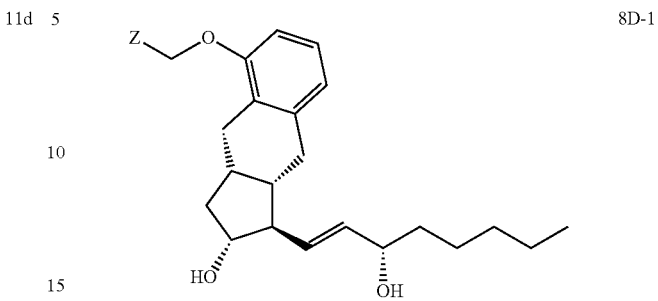

wherein Z is —CN.

The present invention also pertains to a novel compound of Formula 11-1

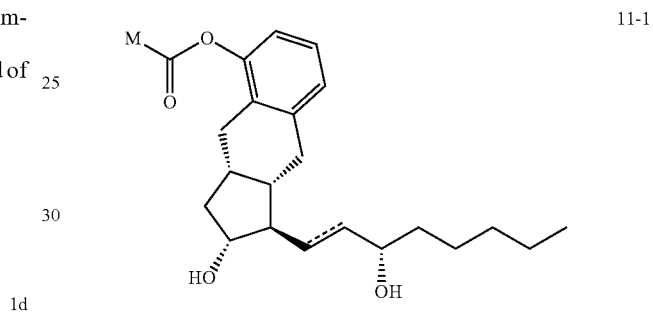

wherein M is methyl, phenyl or 4-phenylphenyl; and ═══ is a single or double bond.

The following examples are used to further illustrate the present invention, but not intended to limit the scope of the present invention. Any modifications or alterations that can be easily accomplished by persons skilled in the art fall within the scope of the disclosure of the specification and the appended claims.

Example 1

(2R,3R,4R)-2-(3-(benzyloxy)benzyl)-4-tert-butyldimethylsilyoxy-3-((S,E)-3-tert-butyldimethylsilyoxyoct-1-enyl)cyclopentanone

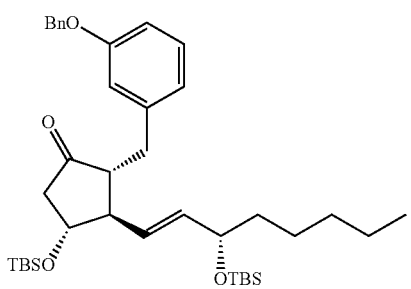 [SMILES: CCCCC[C@@H](/C=C/[C@H]1[C@H](O[Si](C)(C)C(C)(C)C)CC(=O)[C@@H]1Cc1cccc(OCc2ccccc2)c1)O[Si](C)(C)C(C)(C)C]

A 12-liter three-necked flask was flame dried and allowed to be cooled. (1E)-tributyl-stannyl-(3S)-tert-butyldimethylsilyoxyoctene (520 g, 0.98 mol) and 4 liter tetrahydrofuran (THF) were added to the reaction flask, followed by dropwise addition of n-butyl-lithium (612 ml, 1.6M in hexane) at −70° C. A homogenous solution of copper cyanide (87.7 g, 0.98 mol) and methyllithium (490 ml, 2M in ether) in 1 liter THF was cooled from −10° C. to −70° C. and added to the reaction flask while stirring for 30 minutes. Then, a solution of (R)-1-(3-benzyloxy)benzyl-5-oxo-3-tert-butyldimethylsilyoxycyclopentene (200 g, 0.49 mol) in 1 liter THF at −70° C. was added to the reaction mixture for 30 minutes. The reaction was quenched with 5 liter saturated ammonium chloride (aq) containing 500 ml ammonium hydroxide. The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. Yield of the titled compound was 280 g (88%).

$^1$H-NMR (CDCl$_3$): δ 7.43 (d, 2H), 7.39 (t, 2H), 7.32 (t, 1H), 7.16 (t, 1H), 6.81 (d, 1H), 6.78 (s, 1H), 6.73 (d, 1H), 5.55 (dd, 1H), 5.4 (dd, 1H), 5.02 (s, 2H), 4.10~4.02 (m, 2H), 3.05 (d, 1H), 2.80 (d, 1H), 2.60 (d, 1H), 2.42 (dt, 1H), 2.30~2.25 (m, 1H), 2.04 (dd, 1H), 1.47~1.25 (m, 8H), 0.92~0.77 (m, 21H), 0.12~0.01 (m, 12H)

$^{13}$C-NMR (CDCl$_3$): δ 215.40, 158.77, 140.51, 137.08, 136.61, 129.27, 128.52, 128.42, 127.85, 127.44, 122.31, 115.97, 112.84, 73.33, 72.69, 69.78, 55.14, 51.64, 47.68, 38.49, 33.28, 31.85, 25.89, 25.89, 22.62, 18.22, 18.04, 14.05, −4.66, −4.67, −4.71

Example 2

(2R,3R,4R)-2-(3-(benzyloxy)benzyl)-4-triethylsilyoxy-3-((S,E)-3-triethylsilyoxy oct-1-enyl)cyclopentanone

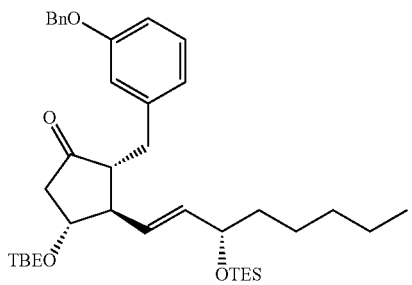

A 2-liter three-necked flask was flame dried and allowed to be cooled. (1E)-tributyl-stannyl-(3S)-triethylsilyoxyoctene (127 g, 0.24 mol) and 1 liter THF were added to the reaction flask, followed by dropwise addition of n-butyl-lithium (150 ml, 1.6M in hexane) at −70° C. A homogenous solution of copper cyanide (21.5 g, 0.24 mol) and methyllithium (120 ml, 2M in ether) in 50 ml THF was cooled from −10° C. to −70° C. and added to the reaction flask while stirring for 30 minutes. Then, a solution of (R)-1-(3-benzyloxy)benzyl-5-oxo-3-triethylsilyoxy-cyclopentene (50 g, 0.12 mol) in 500 ml THF at −70° C. was added to the reaction mixture for 30 minutes. The reaction was quenched with 1.25 liter saturated ammonium chloride (aq) containing 125 ml ammonium hydroxide. The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. Yield of the titled compound was 75 g (94%).

$^1$H-NMR (CDCl$_3$): δ 7.42 (d, 2H), 7.37 (t, 2H), 7.31 (t, 1H), 7.15 (d, 1H), 6.80 (d, 1H), 6.77 (s, 1H), 6.73 (d, 1H), 5.57~5.48 (m, 2H), 5.04 (s, 2H), 4.10~4.02 (m, 2H), 3.06 (dd, 1H), 2.80 (dd, 1H), 2.59 (dd, 1H), 2.45 (dt, 1H), 2.31~2.27 (m, 1H), 2.05 (dd, 1H), 1.49~1.27 (m, 8H), 0.97~0.86 (m, 21H), 0.64~0.55 (m, 12H)

$^{13}$C-NMR (CDCl$_3$) δ 215.50, 158.77, 140.47, 137.07, 136.40, 129.26, 128.51, 128.49, 127.82, 127.42, 122.28, 115.95, 112.81, 73.10, 72.84, 69.76, 55.02, 51.34, 47.79, 38.54, 33.37, 31.86, 25.09, 22.62, 14.04, 6.91, 6.75, 4.99, 4.73

Example 3

(2R,3R,4R)-2-(3-(benzyloxy)benzyl)-4-tert-butyldimethylsilyoxy-3-((S)-3-tert-butyldimethylsilyoxyoctyl)cyclopentanone

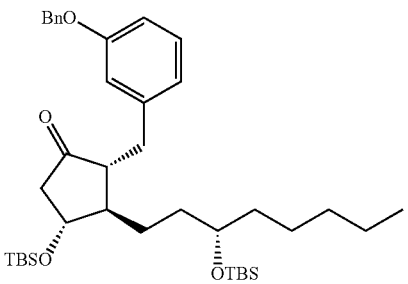 [SMILES: CCCCC[C@@H](CC[C@H]1[C@H](O[Si](C)(C)C(C)(C)C)CC(=O)[C@@H]1Cc1cccc(OCc2ccccc2)c1)O[Si](C)(C)C(C)(C)C]

A 25 ml two-necked flask was flame dried and allowed to be cooled. (S)-tert-butyl(1-iodooctan-3-yloxy)dimethylsilane (1.18 g, 3.2 mmol) and 11.8 L ether were added to the reaction flask, followed by dropwise addition of tert-butyl-lithium (3.75 ml, 1.7M in pentane) at −700° C. A homogenous solution of copper cyanide (0.29 g, 3.2 mmol) and methyllithium (1.6 ml., 2M in ether) in 5.8 ml ether was cooled from room temperature to −70° C. and added to the reaction flask while stirring for 30 minutes. Then, a solution of (R)-2 (3-(benzyloxy)benzyl)-4-tert-butyldimethylsilyloxy)cyclopent-2-enone (0.65 g, 1.6 mmol) in 6.5 ml ether at −70° C. was added to the reaction mixture for 30 minutes. The reaction was quenched with 40 ml saturated ammonium chloride (aq) containing 0.4 ml ammonium hydroxide. The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. Yield of the titled compound was 1.1 g (85%).

$^1$H NMR (500 MHz, CDCl$_3$) δ 0.00~0.10 (12H, m), 0.88~0.91 (21H, m), 1.19~1.49 (12H, m), 1.91 (1H, m), 1.49~2.17 (2H, m), 2.58 (1H, dd, J=6, 17.5 Hz), 2.86 (1H, ab), 3.02 (1H, ab), 3.50 (1H, m), 4.09 (1H, q, J=5.5 Hz), 5.04 (2H, s), 6.77~6.84 (3H, m), 7.19 (1H, t, J=7.5 Hz), 7.33 (1H, m), 7.39 (2H, m), 7.44 (2H, m)

$^{13}$C NMR (125 MHz, CDCl$_3$) δ−4.8, −4.5, −4.43, −4.41, 14.0, 17.9, 18.0, 22.6, 24.8, 25.8, 25.9, 27.9, 32.0, 33.9, 35.9, 37.1, 47.5, 48.7, 54.8, 69.8, 72.3, 73.4, 112.7, 115.7, 121.9, 127.4, 127.8, 128.5, 129.4, 137.0, 141.3, 158.8, 217.6

Example 4

(2R,3R,4R)-2-(3-(tert-butyldimethylsilyoxy)benzyl)-4-(tetrahydro-2H-pyran-2-yloxy)-3-((S,E)-3-(tetrahydro-2H-pyran-2-yloxy)oct-1-enyl)cyclopentanone

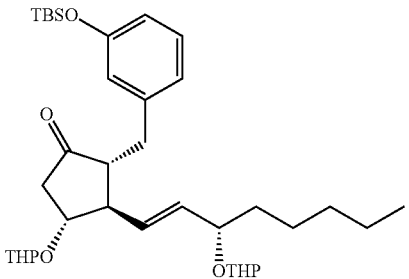

A 2-liter three-necked flask was flame dried and allowed to be cooled. (1E)-Iodo-(3,S)-(tetrahydro-2H-pyran-2-yloxy)-1-octene (5.84 g, 17 mmol) and 50 ml ether were added to the reaction flask, followed by dropwise addition of n-butyl-lithium (12 ml, 1.6M in hexane) at −70° C. A previously prepared solution of 2.35 g of pentynyl-copper with 5.87 g of tris(dimethylamino)phosphine in 30 ml ether was added. The mixture was kept at this temperature for a further 30 min, in a solution of (R)-1-(3-(tert-butyldimethylsilyoxy)benzyl)-5-oxo-3-(tetrahydro-2H-pyran-2-yloxy)-cyclopentene (5.66 g, 15 mmol) in 500 ml THF at −70° C. was added to the reaction mixture for 30 minutes. The reaction was quenched with 100 ml saturated ammonium chloride (aq) containing 10 ml ammonium hydroxide. The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. Yield of the titled compound was 6.65 g (75%).

Example 5

((S,E)-1-((1R,2R,5R)-2-(3-(benzyloxy)benzyl)-3-methylene-5-(tert-butyldimethylsilyoxy)cyclopentyl) oct-1-en-3-yloxy)(tert-butyl)dimethylsilane

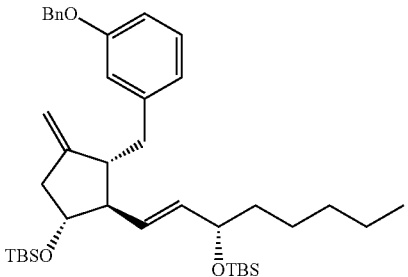 [SMILES: C=C1C[C@@H](O[Si](C)(C)C(C)(C)C)[C@H](/C=C/[C@H](CCCCC)O[Si](C)(C)C(C)(C)C)[C@H]1Cc1cccc(OCc2ccccc2)c1]

A methylenelation solution of Zn—CH$_2$Br$_2$—TiCl$_4$ (500 ml, 0.6M in THF) and 100 ml dichloromethane (CH$_2$Cl$_2$) were added to 5 liter three-necked flask in ice-water bath. To the stirred mixture was added (2R,3R,4R)-2-(3-(benzyloxy)benzyl)-4-tert-butyl dimethylsiloxy-3-((S,E)-3-tert-butyldimethylsilyoxy oct-1-enyl)cyclopentanone (200 g, 0.307 mol) in 1 liter CH$_2$Cl$_2$. After 10 minutes, the cooling bath was removed and the mixture was stirred at room temperature (25° C.) for 1.5 hr. Then, the mixture was diluted with 1 liter ethyl acetate and 500 ml saturated sodium bicarbonate aqueous. The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. Yield of the titled compound was 179.4 g (90%).

$^1$H-NMR (CDCl$_3$): δ 7.44 (d, 2H), 7.39 (t, 2H), 7.33 (t, 1H), 7.17 (t, 1H), 6.84 (s, 1H), 6.80 (d, 2H), 5.48~5.39 (m, 2H), 5.04 (s, 2H), 4.88 (s, 1H), 4.66 (s, 1H), 4.04 (q, 1H), 3.87 (q, 1H), 2.95 (dd, 1H), 2.68 (dd, 1H), 2.51~2.47 (m, 1H), 2.31~2.21 (m, 2H), 1.32~1.26 (m, 8H), 0.91~0.86 (m, 21H), 0.05~0.01 (m, 12H)

$^{13}$C-NMR (CDCl$_3$): δ 158.64, 150.94, 142.36, 137.18, 135.20, 130.20, 128.98, 128.51, 127.83, 127.43, 122.22, 116.04, 112.11, 107.01, 72.95, 69.82, 55.70, 48.03, 42.73, 39.20, 38.57, 31.85, 25.92, 25.89, 25.14, 22.83, 18.23, 18.11, 14.06, −4.17 4.56, −4.74

Example 6

((S)-1-((1R,2R,5R)-2-(3-(benzyloxy)benzyl)-3-methylene-5-(tert-butyldimethylsilyoxy)cyclopentyl) octan-3-yloxy)(tert-butyl)dimethylsilane

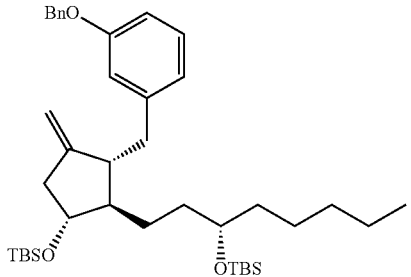 [SMILES: C=C1C[C@@H](O[Si](C)(C)C(C)(C)C)[C@H](CC[C@H](CCCCC)O[Si](C)(C)C(C)(C)C)[C@H]1Cc1cccc(OCc2ccccc2)c1]

A methylenelation solution of Zn—CH$_2$Br$_2$—TiCl$_4$ (6 ml, 0.6M in THF) and 3.3 ml dichloromethane (CH$_2$Cl$_2$) were added to 25 ml two-necked flask in ice-water bath. To the stirred mixture was added (2R,3R,4R)-2-(3-(benzyloxy)benzyl)-4-(tert-butyldimethylsilyloxy)-3-((S)-3-(tert-butyldimethylsilyloxy)octyl)cyclopentanone (1.1 g, 1.68 mmol) in 10 ml CH$_2$Cl$_2$. After 10 minutes, the cooling bath was removed and the mixture was stirred at room temperature (25° C.) for 1.5 hr. Until the reaction was completed, the mixture was diluted with 20 ml EtOAc and was filtered to remove the precipitate. The filtrate was extracted with EtOAc, dried over MgSO$_4$, and evaporated. The resulting residue was purified by chromatography on a silica gel column using hexane-EtOAc as eluent to give the titled compound: 0.85 g (yield: 78%)

$^1$H NMR (500 MHz, CDCl$_3$) δ 0.00~0.12 (12H, m), 0.90~0.94 (21H, m), 1.26~0.46 (12H, m) 1.68 (1H, m), 2.32~2.40 (2H, m), 2.58 (1H, dd, J=6, 15.5 Hz), 2.79~2.91 (2H, m), 3.53 (1H, m), 3.85 (1H, q, J=5.5 Hz), 4.68 (1H, s), 4.90 (1H, s), 5.07 (2H, s), 6.82~6.88 (3H, m), 7.21 (1H, t, J=7.5 Hz), 7.35 (1H, m), 7.41 (2H, t, J=7 Hz), 7.47 (2H, m)

$^{13}$C NMR (125 MHz, CDCl$_3$) δ –4.7, –4.41, –4.38, 14.1, 18.0, 18.2, 22.7, 25.0, 25.5, 25.9, 28.6, 32.1, 34.6, 37.1, 41.9, 42.6, 49.1, 52.3, 69.8, 72.3, 72.6, 107.5, 112.1, 116.0, 122.1, 127.4, 127.8, 128.5, 129.0, 137.2, 142.8, 152.4, 158.7

Example 7

(1R,2R,3R)-3-(3-(benzyloxy)benzyl-2-((S,E)-3-hydroxyoct-1-enyl)-4-methylenecyclopentanol

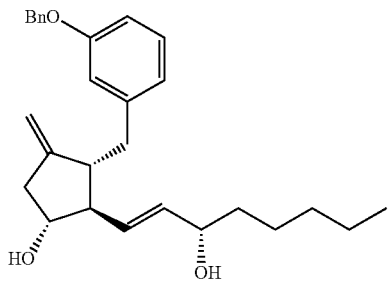 [SMILES: C=C1C[C@@H](O)[C@H](/C=C/[C@@H](O)CCCCC)[C@H]1Cc1cccc(OCc2ccccc2)c1]

A solution of Zn—CH$_2$Br$_2$—TiCl$_4$ (80 ml, 0.6M in THF) and 10 ml dichloromethane (CH$_2$Cl$_2$) were added to 500 ml three-necked flask in ice-water bath. To the stirred mixture was added (1R,2R,3R)-1-(3-benzyloxy)benzyl-5-oxo-3-triethylsilyoxy-2-[(3)-triethylsilyoxy-1-octenyl]-cyclopentane (20 g, 30.7 mmol) in 100 ml CH$_2$Cl$_2$. After 10 minutes, the cooling bath was removed and the mixture was stirred at room temperature (25° C.) for 1.5 hr. Then, the mixture was diluted with 150 ml ethyl acetate and 50 ml saturated sodium bicarbonate aqueous. The reaction mixture was phase separated and the aqueous layer was extracted with ethyl acetate. The organic layers were combined and dried over anhydrous magnesium sulfate. The solid was filtered off. The solvent was evaporated off under vacuum. The residue was further dissolved in 100 ml acetone and 20 ml water, followed by addition of 0.5 g p-toluenesulfonic acid monohydrate. The reaction solution was stirred at room temperature for 1 hour and further subjected to vacuum evaporation until two separate layers were formed. 1.5 L ethyl acetate was added to the reaction and the reaction was allowed to be phase separated. The organic layer was washed with saturated sodium bicarbonate solution and brine, dried over anhydrous magnesium sulfate, and evaporated to dryness. The crude product was purified by chromatography on silica gel using a mixture of hexane and ethyl acetate as a gradient eluent. Yield of the titled compound was 12.83 g containing a trace amount of 15-epimer. The 15-epimer was removed by crystallization from ether/hexane. 9.7 g titled compound was obtained in a crystalline form (white to off-white powder). MP: 58° C.

$^1$H-NMR (CDCl$_3$): δ 7.43 (d, 2H), 7.38 (t, 2H), 7.32 (t, 1H), 7.15 (t, 1H), 6.81~6.76 (m, 3H), 5.45~5.29 (m, 2H), 5.03 (s, 2H), 4.95 (s, 1H), 4.81 (s, 1H), 3.92 (q, 1H), 3.80 (q, 1H), 2.85~2.69 (m, 3H), 2.55~2.52 (m, 1H), 2.30~2.24 (m, 1H), 2.10 (q, 1H), 1.45~1.25 (m, 8H), 0.87 (t, 3H)

$^{13}$C-NMR (CDCl$_3$): δ 158.68, 149.97, 141.77, 137.08, 135.83, 132.14, 129.02, 128.55, 127.90, 127.45, 122.24, 116.22, 112.19, 107.76, 75.33, 72.73, 69.86, 56.67, 48.11, 41.09, 39.13, 37.14, 31, 73, 25.16, 22.59, 14.03

Example 8

((S,E)-1-((1R,2R,5R)-2-(3-(benzyloxy)benzyl)-3-methylene-5-(tert-butyldimethylsilyoxy)cyclopentyl)oct-1-en-3-yloxy)(tert-butyl)dimethylsilane

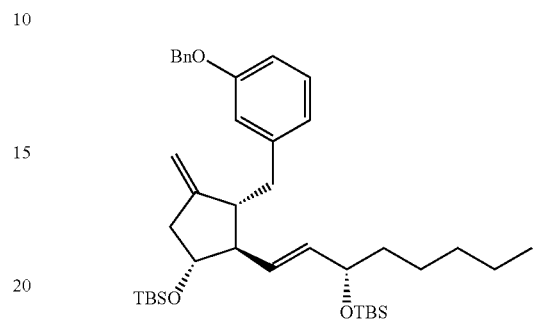

(1R,2R,3R)-3-(3-(benzyloxy)benzyl)-2-((S,E)-3-hydroxyoct-1-enyl)-4-methylenecyclopentanol (12.7 g, 64 mmol) was dissolved in 300 ml ethyl acetate, added with imidazole (22 g, 320 mmol), and stirred until the reaction system became homogeneous. Tert-butyldimethylsilyl chloride (24 g, 160 mmol) was added into the reaction mixture. The stirred reaction mixture was brought to room temperature and stirred overnight. Subsequently, the reaction mixture was washed with 300 ml saturated sodium bicarbonate aqueous solution twice, further washed with brine, dried over anhydrous magnesium sulfate, filtered, and concentrated to obtain the crude product. The crude product was purified by chromatography on silica gel using a mixture of hexane and ethyl acetate as a gradient eluent. Yield: 80%.

$^1$H-NMR (CDCl$_3$): δ 7.44 (d, 2H), 7.39 (t, 2H), 7.33 (t, 1H), 7.17 (t, 1H), 6.84 (s, 1H), 6.80 (d, 2H), 5.48~5.39 (m, 2H), 5.04 (s, 2H), 4.88 (s, 1H), 4.66 (s, 1H), 4.04 (q, 1H), 3.87 (q, 1H), 2.95 (dd, 1H), 2.68 (dd, 1H), 2.60 (dd, 1H), 2.51~2.47 (m, 1H), 2.31~2.21 (m, 2H), 1.32~1.26 (m, 8H), 0.91~0.86 (m, 2H) 0.05~0.01 (m, 12H)

$^{13}$C-NMR (CDCl$_3$): δ 158.64, 150.94, 142.36, 137.18, 135.20, 130.20, 128.98, 128.51, 127.83, 127.43, 122.22, 116.04, 112.11, 107.01, 72.95, 69.82, 55.70, 48.03, 42.73, 39.20, 38.57, 31.85, 25.92, 25.89, 25.14, 22.83, 18.23, 18.11, 14.06, –4.17, –4.56, –4.74

Example 9

((1S,2S,3R,4R)-2-(3-(benzyloxy)benzyl)-4-(tert-butyldimethylsilyoxy)-3-((S,E)-3-(tert-butyldimethylsilyoxy)oct-1-enyl)cyclopentyl)methanol

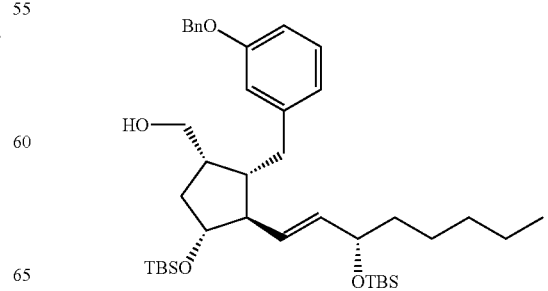

A degassed solution of (1R,2R,3R)-1-(3-benzyloxy)benzyl-3-tert-butyl-di-methylsilyoxy-2-[(3S)-tert-butyldimethylsilyoxy-1-octenyl]-5-methylene-cyclopentane (160 g, 0.246 mol) in 1.6 liter dry THF was cooled to 0° C., under nitrogen, added with 9-borabicyclo[3,3,1]nonane (1280 ml, 0.5M in THF), dropwise over 5 min. The colorless solution was stirred for overnight at 0° C. and treated with 30% hydrogen peroxide (640 ml) followed by 3N potassium hydroxide (640 ml). The resulting suspension was stirred for an additional 30 min at 0° C., and for 75 min while warming to room temperature. The reaction mixture was transferred to a separatory funnel, diluted with 3 liter brine and 1 liter ethyl acetate. The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. Yield: 97%.

$^1$H-NMR (CDCl$_3$): δ 7.45~7.29 (m, 5H), 7.17 (t, 1H), 6.83~6.77 (m, 3H), 5.50~5.35 (m, 2H), 5.03 (s, 2H), 4.13~4.02 (m, 2H), 3.77 (t, 1H), 3.61 (d, 1H), 3.42 (d, 1H), 2.80~2.75 (m, 1H), 2.43~2.39 (m, 2H), 2.05~1.86 (m, 4H), 1.66~1.26 (m, 8H), 0.90~0.84 (m, 21H), 0.08~000 (m, 12H)

$^{13}$C-NMR (CDCl3): δ 158.74, 143.51, 137.07, 135.03, 131.13, 129.22, 128.52, 127.86, 127.43, 121.30, 115.22, 111.826 79.11, 73.05, 69.80, 63.62, 58.59, 49.44, 41.45, 40.58, 38.63, 31.83, 25.91, 25.76, 25.12, 22.64, 18.29, 17.87, 14.66, −4.22, −445, −4.83

Example 10

((1S,2S,3R,4R)-2-(3-(benzyloxy)benzyl)-4-(tert-butyldimethylsilyoxy)-3-((S)-3-(tert-butyl dimethyl-silyoxy)octyl)cyclopentyl)methanol

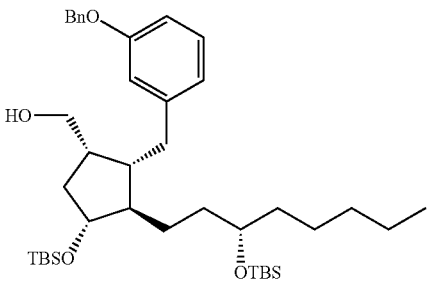 [SMILES: CCCCC[C@@H](CC[C@@H]1[C@@H](Cc2cccc(OCc3ccccc3)c2)[C@@H](CO)C[C@H]1O[Si](C)(C)C(C)(C)C)O[Si](C)(C)C(C)(C)C]

A degassed solution of ((1R,2R,3R)-3-(3-(benzyloxy)benzyl)-2-((S)-3-(tert-butyldimethylsilyloxy)octyl)-4-methylenecyclopentyloxy)(tert-butyl)dimethylsilane (0.75 g, 1.15 mmol) in 8 ml dry THF was cooled to 0° C. under nitrogen, and 9-borabicyclo[3,3,1]nonane (6.9 ml, 0.5M in THF) was dropwise added to the mixture. The colorless solution was stirred for overnight at 0° C. and treated with 30% hydrogen peroxide (3 ml) followed by 3N potassium hydroxide (3 ml). The resulting suspension was stirred for one hour at room temperature. The mixture was extracted with EtOAc, and the organic layer was washed with 20 ml brine, dried over MgSO$_4$, and evaporated. The resulting residue was purified by chromatography on a silica gel column using hexane-EtOAc as eluent to give the titled compound: 0.6 g (yield 78%)

$^1$H NMR (500 MHz, CDCl$_3$) δ 0.02~0.12 (12H, m), 0.90~0.92 (2H, m), 1.22~1.43 (9H, m), 1.55~1.57 (2H, m), 1.72~1.74 (2H, m), 1.92~2.07 (4H, m), 2.80~2.94 (2H, m), 3.50~3.57 (2H, m), 3.63 (1H, dd, J=3, 11 Hz), 3.76 (1H, br) 3.96 (1H, d, J=6.5 Hz), 5.05 (2H, s), 6.81 (1H, dd, J=2, 8 Hz), 6.87 (2H, m), 7.19 (1H, t, J=8 Hz), 7.33 (1H, m), 7.39 (2H, t, J=7.5 Hz), 7.44 (2H, m)

$^{13}$C NMR (125 MHz, CDCl$_3$) δ−4.7, −4.5, −4.43, −4.41, 14.0, 17.8, 18.1, 22.6, 24.8, 25.7, 25.9, 29.9, 32.0, 35.2, 35.9, 37.1, 40.2, 42.5, 48.5, 54.9, 63.7, 69.8, 72.5, 79.2, 111.9, 115.3, 121.4, 127.4, 127.8, 128.5, 129.2, 137.1, 143.7, 158.8

Example 11

((1S,2S,3R,4R)-2-(3-(benzyloxy)benzyl)-4-(tert-butyldimethylsiloxy)-3-((S,E)-3-(tert-butyldimethylsilyoxy)oct-1-enyl)cyclopentyl)methyl methanesulfonate

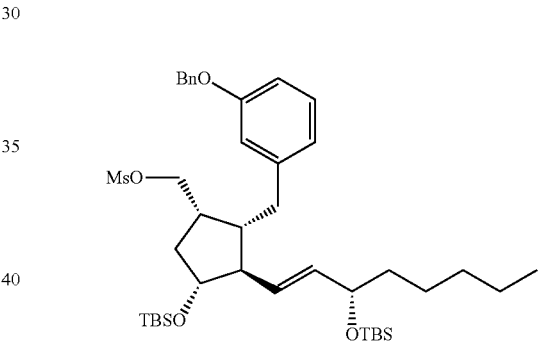

A solution of ((1S,2S,3R,4R)-2-(3-(benzyloxy)benzyl)-4-(tert-butyldimethysilyoxy)-3-((S,E)-3-(tert-butyldimethylsilyoxy)oct-1-enyl)cyclopentyl)methanol (50 g, 0.075 mol) in dry CH$_2$Cl$_2$ (500 ml) was cooled to 0° C. under nitrogen and treated with triethylamine (31.3 ml, 0.225 mol), then with methanesulfonyl chloride (11.6 ml, 0.15 mol). The mixture was poured to saturated sodium bicarbonate aqueous and stirred for 30 minutes. The reaction mixture was phase separated and the aqueous layer was extracted with 500 ml ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. Yield: 81%.

$^1$H-NMR (CDCl$_3$): δ 7.45~7.29 (m, 5H), 7.19 (t, 1H), 6.82~6.78 (m, 3H), 5.48~55.33 (m, 2H), 5.05 (s, 2H), 4.38 (dd, 1H), 4.28~4.22 (m, 1H), 4.05~3.96 (m, 2H), 2.89 (s, 3H), 2.80 (dd, 1H), 2.52 (dd, 1H), 2.29~2.20 (m, 1H), 2.11~2.02 (m, 1H), 1.68~1.59 (m, 2H), 1.44~1.24 (m, 8H), 0.89~0.67 (m, 21H), 0.07~0.00 (m, 12H)

Example 12

((1S,2S,3R,4R)-2-(3-(benzyloxy)benzyl)-4-(tert-butyldimethylsilyoxy)-3-((S,E)-3-(tert-butyldimethylsilyoxy)oct-1-enyl)cyclopentyl)methyl 4-methylbenzenesulfonate

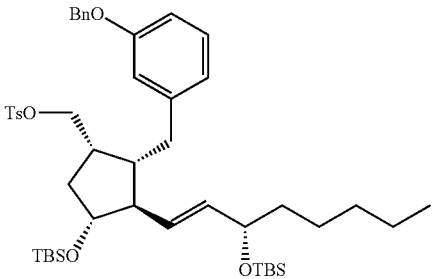 [SMILES: CCCCC[C@@H](/C=C/[C@@H]1[C@@H](Cc2cccc(OCc3ccccc3)c2)[C@@H](COS(=O)(=O)c2ccc(C)cc2)C[C@H]1O[Si](C)(C)C(C)(C)C)O[Si](C)(C)C(C)(C)C]

A solution of ((1S,2S,3R,4R)-2-(3-(benzyloxy)benzyl)-4-(ter-butyldimethylsilyoxy)-3-((S,E)-3-(tert-butyldimethylsilyoxy)oct-1-enyl)cyclopentyl)methanol (15 g, 0.023 mol) in dry $CH_2Cl_2$ (500 ml) was cooled to 0° C. under nitrogen and treated with triethylamine (9.6 ml, 0.068 mol), then with p-Toluenesulfonic chloride (8.77 g, 0.046 mol). The mixture was poured to saturated sodium bicarbonate aqueous and stirred for 30 minutes. The reaction mixture was phase separated and the aqueous layer was extracted with 500 ml ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. Yield: 85%.

$^1$H-NMR (CDCl$_3$): δ 7.72 (d, 2H), 7.46~7.29 (m, 8H), 7.13 (t, 1H), 6.80~6.64 (m, 3H), 5.57~5.32 (m, 2H), 5.04 (s, 2H), 4.15~3.88 (m, 4H), 2.67 (dd, 1H), 2.41 (m, 4H), 2.17~1.94 (m, 4H), 1.49~1.28 (m, 8H), 0.92~0.82 (m, 21H), 0.04~0.00 (m, 12H)

$^{13}$C-NMR (CDCl$_3$): δ 158.86, 144.53, 142.20, 137.10, 135.60, 133.05, 130.20, 129.78, 128.53, 127.88, 127.86, 127.48, 121.19, 115.06, 112.23, 78.00, 72.87, 69.83, 56.22, 46.62, 38.56, 38.00, 37.85, 34.50, 31.81, 25.88, 25.83, 25.62, 25.06, 22.61, 21.59, 18.22, 17.93, 14.03–4.23, –4.61, –4.77

Example 13

((1S,2S,3R,4R)-2-(3-(benzyloxy)benzyl)-4-(tert-butyldimethylsilyoxy)-3-((S)-3-(tert-butyl dimethylsilyoxy)octyl)cyclopentyl)methyl 4-methylbenzenesulfonate

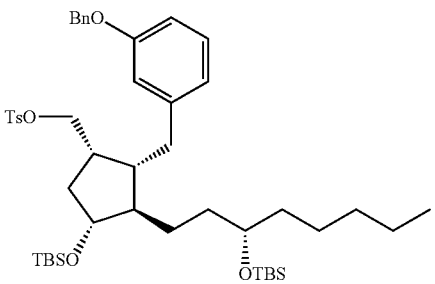 [SMILES: CCCCC[C@@H](CC[C@@H]1[C@@H](Cc2cccc(OCc3ccccc3)c2)[C@@H](COS(=O)(=O)c2ccc(C)cc2)C[C@H]1O[Si](C)(C)C(C)(C)C)O[Si](C)(C)C(C)(C)C]

A solution of ((1S,2S,3R,4R)-2-(3-(benzyloxy)benzyl)-4-(tert-butyldimethylsilyloxy)-3-(S)-3-((tert-butyldimethylsilyloxy)octyl)cyclopentyl)methanol (0.3 g, 0.45 mmol) in dry $CH_2Cl_2$ (3 ml) was cooled to 0° C. under nitrogen and treated with triethylamine (0.12 ml, 0.9 mmol) and trace amount 4-(dimethylamino)pyridine (DMAP), then p-toluenesulfonyl chloride (0.13 g, 0.67 mmol) was added and the reaction was stirred at room temperature. After the reaction was completed, 20 ml saturated NaHCO$_3$ was added, and extracted with CH$_2$Cl$_2$, dried over MgSO$_4$, and evaporated. The resulting residue was purified by chromatography on a silica gel column using hexane-EtOAc as eluent to give the titled compound 0.2 g, yield 54%.

$^1$H NMR (500 MHz, CDCl$_3$) δ–0.03~0.04 (12H, m), 0.85~0.90 (21H, m), 1.06~1.09 (2H, m), 1.17~1.30 (8H, m), 1.48 (1H, m), 1.55 (1H, m), 1.90~1.95 (3H, m), 2.28 (1H, q, J=7 Hz), 2.41 (3H, s), 2.49~2.59 (3H, m), 3.45 (1H, m), 3.82 (1H, m), 4.07~4.18 (2H, m), 5.04 (2H, s), 6.70 (1H, d, J=7.5 Hz), 6.76 (1H, s), 6.79 (1H, m), 7.15 (1H, t, J=8 Hz), 7.29~7.34 (3H, m), 7.39 (2H, t, J=5.5 Hz), 7.45 (2H, m), 7.65 (2H, d, J=8 Hz)

$^{13}$C NMR (125 MHz, CDCl$_3$) δ–4.8, –4.45, –4.41, 14.0, 17.8, 18.1, 21.6, 22.6, 24.8, 25.82, 25.88, 25.91, 29.0, 32.0, 34.8, 35.5, 37.1, 37.9, 39.2, 46.4, 52.7, 69.8, 71.8, 72.4, 78.3 112.2, 115.4, 121.6, 127.4, 127.9, 128.51, 128.54, 129.2, 129.8, 133.0, 137.1, 142.4, 144.6, 158.8

Example 14

((1S,2S,3R,4R)-2-(3-hydroxybenzyl)-4-(tert-butyldimethylsilyoxy)-3-((S,E)-3-(tert-butyl dimethylsilyoxy)oct-1-enyl)cyclopentyl)methyl methanesulfonate

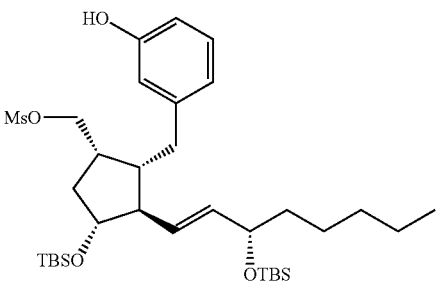 [SMILES: CCCCC[C@@H](/C=C/[C@@H]1[C@@H](Cc2cccc(O)c2)[C@@H](COS(C)(=O)=O)C[C@H]1O[Si](C)(C)C(C)(C)C)O[Si](C)(C)C(C)(C)C]

A solution of ((1S,2S,3R,4R)-2-(3-(benzyloxy)benzyl)-4-(tert-butyldimethylsilyoxy)-3-(S,E)-3-(tert-butyldimethylsilyloxy)oct-1-enyl)cyclopentyl)methyl methanesulfinate (45 g, 0.06 mol) in dry methanol (450 ml) was treated with potassium hydroxide (9.72 g, 0.18 mol), then with 5% Pd/C (13.5 g, 30% wt) under hydrogen for 2 hr. Then, the reaction mixture was filtered with celite pad. The filtrate was concentrated to obtain crude product (50 g).

$^1$H-NMR (CDCl$_3$): δ 7.11 (t, 1H), 6.73 (d, 1H), 6.68 (s, 1H), 6.64 (d, 1H), 5.45~5.34 (m, 2H), 5.28 (br s, 1H), 4.28~4.24 (m, 1H), 4.10~4.02 (m, 2H), 3.97~3.93 (m, 1H), 2.71 (dd, 1H), 2.53 (dd, 1H), 2.26~2.22 (m, 2H), 2.05~1.98

(m, 5H), 1.61~1.57 (m, 1H), 1.44~1.25 (m, 10H), 0.92~0.85 (m, 21H), 0.11~0.02 (m, 12H)

Example 15

((1S,2S,3R,4R)-2-(3-hydroxybenzyl)-4-(tert-butyldimethylsilyoxy)-3-((S,E)-3-(tert-butyl dimethylsilyoxy)oct-1-enyl)cyclopentyl)methyl 4-methylbenzenesulfonate

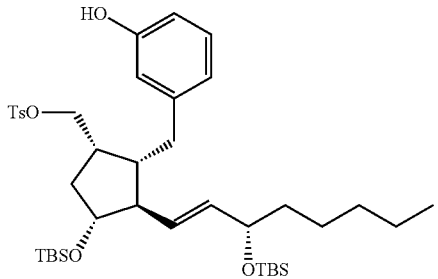

A solution of ((1S,2S,3R,4R)-2-(3-(benzyloxy)benzyl)-4-(tert-butyldimethylsilyoxy)-3-((S,E)-3-(tert-butyldimethylsilyoxy)oct-1-enyl)cyclopentyl)methyl 4-methylbenzenesulfonate (15.7 g, 0.019 mol) in dry methanol (150 ml) was treated with potassium hydroxide (3.25 g, 0.057 mol), then with 5% Pd/C (6.28 g, 40% wt) under hydrogen for 5 hr. Then, the reaction mixture was filtered with celite pad. The solvent was evaporated off under vacuum. The crude product was purified by chromatography on silica gel using a mixture of hexane and ethyl acetate as a gradient eluent. Yield: 90%

¹H-NMR (CDCl₃): δ 7.81 (d, 2H), 7.35 (d, 2H), 7.05 (t, 1H), 6.69 (d, 1H), 6.66 (d, 1H), 6.06 (s, 1H), 5.79~5.68 (m, 2H), 4.19~4.16 (m, 1H), 4.01~3.95 (m, 2H), 3.34 (t, 1H), 2.77 (dd, 1H), 2.64 (t, 1H), 2.45~2.39 (m, 4H), 2.18~2.13 (m, 1H), 2.08~2.00 (m, 2H), 1.78~1.73 (m, 1H), 1.68~1.16 (m, —I), 1.41~21 (m, 8H), 0.91~0.81 (m, 21H), 0.10~0.01 (m, 12H)

Examples 16 &, 17

((1S,2S,3R,4R)-2-(3-hydroxybenzyl)-4-(tert-butyldimethylsilyoxy)-3-((S)-3-(tert-butyldimethylsilyoxy)octyl)cyclopentyl)methyl 4-methylbenzenesulfonate

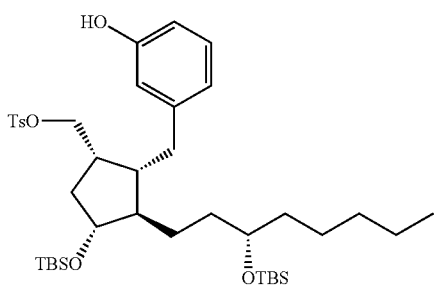 [SMILES: CCCCC[C@@H](CC[C@@H]1[C@@H](Cc2cccc(O)c2)[C@@H](COS(=O)(=O)c2ccc(C)cc2)C[C@H]1O[Si](C)(C)C(C)(C)C)O[Si](C)(C)C(C)(C)C]

Example 16

A solution of ((1S,2S,3R,4R)-2-(3-(benzyloxy)benzyl)-4-(tert-butyl dimethylsilyoxy)-3-((S,E)-3-(tert-butyldimethylsilyoxy)oct-1-enyl)cyclopentyl)methyl 4-methylbenzenesulfonate (15.7 g, 0.019 mol) in dry methanol (150 ml) was treated with potassium hydroxide (3.25 g, 0.057 mol), then with 5% Pd/C (6.28 g, 40% wt) under hydrogen for 6 hr. at room temperature and 24 hr. at 50° C. Then, the reaction mixture was filtered with celite pad. The solvent was evaporated off under vacuum. The crude product was purified by chromatography on silica gel using a mixture of hexane and ethyl acetate as a gradient eluent. Yield: 72%

Example 17

A solution of ((1S,2S,3R,4R)-2-(3-(benzyloxy)benzyl)-4-(tert-butyl dimethylsilyloxy)-3-((S)-3-(tert-butyldimethylsilyloxy)octyl)cyclopentyl)methyl 4-methylbenzenesulfonate (0.15 g, 0.18 mmol) in dry methanol (2 ml) was treated with potassium hydroxide (0.03 g, 0.54 mmol), then 5% Pd/C (0.045 g, 30% wt) under hydrogen for 2 hrs. at room temperature. After the reaction was completed, the mixture was filtered with celite pad, and the filtrate was evaporated. The resulting residue was purified by chromatography on a silica gel column using hexane-EtOAc as eluent, to give the titled compound 0.12 g, yield 90%.

¹H NMR (500 MHz, CDCl₃) δ –0.01~0.10 (12H, m), 0.79~0.91 (21H, m), 1.12~1.46 (12H, m), 1.90 (1H, m), 2.02 (1H, m), 2.28 (1H, m), 2.31 (1H, s), 2.43 (3H, s), 2.54~2.72 (3H, m), 3.49~3.58 (2H, m), 3.91 (1H, m), 4.08 (1H, m), 6.60~6.72 (3H, m), 7.11 (1H, m), 7.22 (1H, d, J=10 Hz), 7.32 (1H, m), 7.72~7.78 (21H, m)

¹³C NMR (125 MHz, CDCl₃) δ –43, –3.6, –3.0, 14.1, 18.0, 18.1, 22.6, 22.7, 25.2, 25.3 25.7, 25.8, 30.3, 31.9, 35.1, 35.6, 37.3, 37.4, 41.0, 48.3, 51.1, 66.5, 71.8, 80.0, 113.0, 115.8, 120.9, 126.7, 127.8, 129.6, 129.89, 129.93, 143.7, 155.9

Examples 18 &19

(1R,2R,3aS,9aS)-2,3,3a,4,9,9a-hexahydro-2-(tert-butyldimethylsilyoxy)-1-((S,E)-3-(tert-butyldimethylsilyoxy)oct-1-enyl)-1H-cyclopenta[b]naphthalen-5-ol

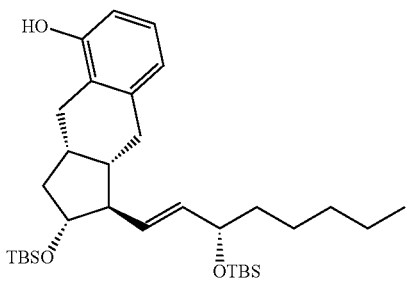 [SMILES: CCCCC[C@@H](/C=C/[C@@H]1[C@H]2Cc3cccc(O)c3C[C@H]2C[C@H]1O[Si](C)(C)C(C)(C)C)O[Si](C)(C)C(C)(C)C]

Example 18

A degassed solution of ((1S,2S,3R,4R)-2-(3-hydroxybenzyl)-4-(tert-butyldimethylsilyoxy)-3-((S,E)-3-(tert-butyldimethylsilyoxy)oct-1-enyl)cyclopentyl)methyl methanesulfonate (50 g, crude compound) in anhydrous glyme (500 ml) at –40° C. under nitrogen was treated with 60% sodium hydride (7.2 g, 0.18 mol). The resulting suspension was then stirred for 40 min at –40° C. then 15 min at 0° C. The suspension was stirred for an additional 20 min while warming to room temperature and then stirred for 2.5 hr at reflux.

The reaction was then cooled to 10° C., diluted with ice cold brine (250 ml) and ethyl acetate (500 ml). The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. Yield: 75%.

Example 19

A degassed solution of ((1S,2S,3R,4R)-2-(3-hydroxybenzyl)-4-(tert-butyldimethylsilyoxy)-3-(S,E)-3-(tert-butyldimethylsilyoxy)oct-1-enyl)cyclopentyl)methyl 4-methylbenzenesulfonate (12.6 g, 0.017 mol) in anhydrous THF (250 ml) at 0° C. under nitrogen was treated with 60% sodium hydride (2.04 g, 0.051 mol). The resulting suspension was stirred for 4 hr at reflux. The reaction is then cooled to 10° C., diluted with ice cold brine (250 ml) and ethyl acetate (500 ml). The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. Yield: 90%.

$^1$H-NMR (CDCl$_3$): δ 7.00 (t, 1H), 6.69 (d, 1H), 6.65 (d, 1H), 5.48~5.46 (m, 2H), 4.70 (br s, 1H), 4.11~4.08 (m, 1H), 3.78~3.75 (m, 1H), 2.70~2.62 (m, 2H), 2.52~2.38 (m, 2H), 2.38~2.20 (m, 1H), 2.6~2.04 (m, 2H), 2.02~1.81 (m, 2H), 1.42~1.25 (m, 8H), 0.90~0.84 (m, 21H), 0.06~0.00 (m, 12H)

$^{13}$C-NMR (CDCl$_3$): δ 152.40, 140.99, 135.10, 130.58, 126.23, 124.44, 120.71, 112.90, 73.08, 55.86, 41.40, 39.80, 38.65, 32.56, 31.85, 25.94, 25.91, 25.19, 22.65, 18.27, 18.19, 14.07, −4.19, −4.55, −4.73

Example 20

(1R,2R,3aS,9aS)-2,3,3a,4,9,9a-hexahydro-2-(tert-butyldimethylsilyoxy)-1-((S)-3-tert-butyldimethylsilyoxy)octyl)-H-cyclopenta[b]naphthalen-5-ol

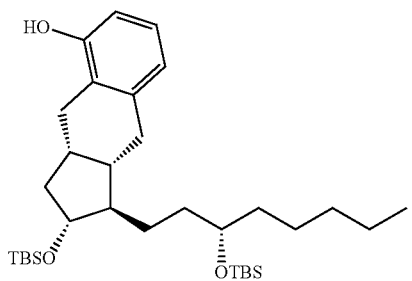 [SMILES: CCCCC[C@@H](CC[C@@H]1[C@H]2Cc3cccc(O)c3C[C@H]2C[C@H]1O[Si](C)(C)C(C)(C)C)O[Si](C)(C)C(C)(C)C]

A degassed solution of ((1S,2S,3R,4R)-2-(3-hydroxybenzyl)-4-(tert-butyldimethylsilyoxy)-3-((S)-3-(tert-butyldimethylsilyoxy)octyl)cyclopentyl)methyl 4-methylbenzenesulfonate (12.4 g, 0.017 mol) in anhydrous THF (250 ml) at 0° C. under nitrogen was treated with 60% sodium hydride (2.04 g, 0.051 mmol). The resulting suspension was stirred for 4 hr at reflux. The reaction was then cooled to 10° C., diluted with ice cold brine (250 ml) and ethyl acetate (500 ml). The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. Yield: 87%.

$^1$H-NMR (CDCl$_3$): δ 7.00 (t, 1H), 6.73 (d, 1H), 6.63 (d, 1H), 4.67 (hr s, 1H), 3.69~3.62 (m, 1H), 2.83~2.74 (m, 2H), 2.49~2.35 (m, 2H), 2.19~2.05 (m, 3H), 1.83~1.81 (m, 1H), 1.43~1.21 (m, 13H), 0.97~0.86 (m, 21H), 0.56~0.00 (m, 12H)

$^{13}$C-NMR (CDCl$_3$): δ 152.06, 141.50, 126.13, 124.72, 120.32, 112.82, 72.76, 52.61, 41.32, 40.42, 37.01, 34.85, 34.31, 33.27, 32.07, 28.01, 26.38, 25.96, 25.90, 24.98, 22.67, 18.17, 18.03, 14.07, −4.25, −4.34, −4.72

Examples 21 & 22

(1R,2R,3aS,9aS)-2,3,3a,4,9,9a-hexahydro-1-((S,E)-3-hydroxyoct-1-enyl)-1H-cyclopenta[b]naphthalene-2,5-diol

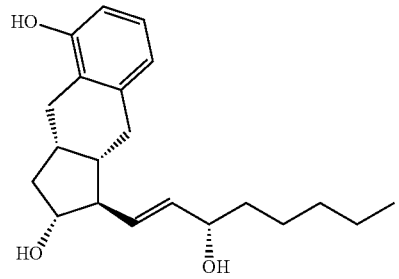 [SMILES: CCCCC[C@H](O)/C=C/[C@@H]1[C@H]2Cc3cccc(O)c3C[C@H]2C[C@H]1O]

Example 21

(1R,2R,3aS,9aS)-2,3,3a,4,9,9a-hexahydro-2-(tert-butyldimethylsilyoxy)-1-((S,E)-3-(tert-butyl dimethylsilyoxy)oct-1-enyl)-1H-cyclopenta[b]naphthalen-5-ol (10 g, 0.018 mmol) was treated with tetrabutylammonium fluoride (180 ml, 1 M in THF) for overnight at room temperature. The reaction mixture was poured to saturated sodium bicarbonate aqueous (200 ml) and stirred for 30 minutes. The reaction mixture was phase separated and the aqueous layer was extracted with 300 ml ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. The titled compound was obtained in a crystalline form. Yield: 70%.

Example 22

(1R,2R,3aS,9aS)-2,3,3a,4,9,9a-hexahydro-2-tert-butyldimethylsilyoxy)-1-((S,E)-3-(tert-butyl dimethylsilyoxy)oct-1-enyl)-1H-cyclopenta[b]naphthalen-5-ol (6.4 g, 0.011 mmol) was dissolved in THF (12.8 ml), then acetic acid (38.4 ml) and distilled water (12.8 ml) for overnight at room temperature. The reaction mixture was poured to saturated sodium bicarbonate aqueous (150 ml) and stirred for 30 minutes. The reaction mixture was phase separated and the aqueous layer was extracted with 200 ml ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. The titled compound was obtained in a crystalline form. (Yield: 88%)

$^1$H-NMR (CDCl$_3$): δ 6.98 (t, 1H), 6.70~6.64 (m, 2H), 5.60 (br s, 1H), 5.53~5.42 (m, 2H), 4.11~4.05 (m, 1H), 3.75~3.66 (m, 1H), 2.64~2.56 (m, 4H), 2.40~2.33 (m, 3H), 2.17~2.16 (m, 1H), 2.05~2.02 (m, 1H), 1.50—1.32 (m, 8H), 1.09~1.05 (m, 1H), 0.90~0.88 (m, 3H)

$^{13}$C-NMR (CDCl$_3$): δ 152.81, 140.47, 135.98, 133.13, 126.26, 124.37, 120.58, 113.18, 75.70, 73.33, 56.52, 45.13, 40.36, 37.10, 32.52, 31.90, 31.66, 25.58, 25.20, 22.61, 14.01

Example 23

(1R,2R,3aS,9aS)-2,3,3a,4,9,9a-hexahydro-2-hydroxy-1-((S,E)-3-hydroxyoct-1-enyl)-1H-cyclopenta[b]naphthalen-5-yl acetate

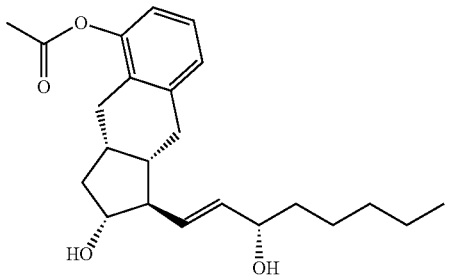 [SMILES: CCCCC[C@H](O)/C=C/[C@@H]1[C@H]2Cc3cccc(OC(C)=O)c3C[C@H]2C[C@H]1O]

(1R,2R,3aS,9aS)-2,3,3a,4,9,9a-hexahydro-2-(tert-butyldimethylsilyoxy)-1-((S,E)-3-(tert-butyldimethylsilyoxy)oct-1-enyl)-1H-cyclopenta[b]naphthalen-5-ol (0.5 g, 0.89 mmol) in toluene (5 ml) was treated with acetic anhydride (0.1 ml, 1.07 mmol) and DMAP (1.1 mg, 0.09 mmol) at room temperature for 30 minutes. The reaction was diluted with saturated sodium bicarbonate aqueous (10 ml) and extracted with ethyl acetate (10 ml). The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. 0.45 g (1R,2R,3aS,9aS)-2,3,3a,4,9,9a-hexahydro-2-(tert-butyldimethylsilyoxy)-1-((S,E)-3-(tert-butyldimethylsilyoxy)oct-1-enyl)-1H-cyclopenta[b]naphthalen-5-yl acetate was obtained. The product was then dissolved in tetrahydrofuran (0.9 ml), and treated with acetic acid (2.7 ml) and distilled water (0.9 ml) overnight at room temperature. The reaction was then diluted with saturated sodium bicarbonate aqueous (12 ml) and extracted with ethyl acetate (15 ml). The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. The titled compound was obtained in a crystalline form. Melting range was 54~65° C. Yield: 65%.

$^1$H-NMR (CDCl$_3$): δ 7.13 (t, 1H), 6.96 (d, 1H), 6.85 (d, 1H), 5.39~5.38 (m, 2H), 3.98~3.93 (m, 1H), 3.62~3.56 (m, 1H), 3.19 (br s, 2H), 2.62 (dd, 1H), 2.50 (dd, 1H), 2.38 (dd, 1H), 2.32~2.24 (m, 5H), 2.14~2.09 (m, 1H), 2.00~1.95 (m, 1H) 1.70~1.66 (m, 1H), 1.55~1.51 (m, 1H), 1.43~1.29 (m, 8H), 1.02 (q, 1H), 0.89 (t, 3H)

$^{13}$C-NMR (CDCl$_3$) δ 169.63, 148.10, 140.71, 136.11, 133.34, 130.57, 126.32, 125.66, 119.47, 75.48, 73.05, 56.65, 40.13, 40.02, 36.89, 32.20, 32.00, 31.64, 27.02, 25.11, 22.55, 20.71, 13.94

Example 24

(1R,2R,3aS,9aS)-2,3,3a,4,9,9a-hexahydro-2-hydroxy-1-((S,E)-3-hydroxyoct-1-enyl)-1H-cyclopenta[b]naphthalen-5-yl benzoate

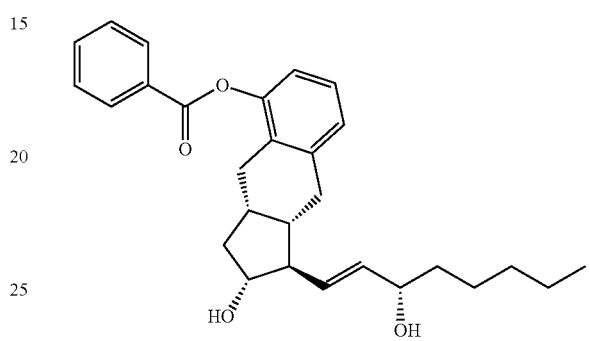

2 g (3.58 mmole, from Example 18) of (1R,2R,3aS,9aS)-2,3,3a,4,9,9a-hexahydro-2-(tert-butyldimethyl-silyoxy)-1-((S,E)-3-(tert-butyldimethylsilyoxy)oct-1-enyl)-1H-cyclopenta[b]naphthalen-5-ol, which contains 6% para-cyclized isomer, in dry tetrahydrofuran (20 ml) was treated with sodium hydride (0.29 g, 7.16 mol) at 0° C. and stirred for 10 minutes at room temperature, followed by dropwise addition of benzoyl chloride (0.63 ml, 5.37 mmol). After 30 minutes, the reaction was cooled to 10° C., diluted with ice cold brine (10 ml) and extracted with ethyl acetate (10 ml). The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. 2.1 g of (1R,2R,3aS,9aS)-2,3,3a,4,9,9a-hexahydro-2-(tert-butyldimethylsilyoxy)-1-((S,E)-3-(tert-butyldimethylsilyoxy)oct-1-enyl)-1H-cyclopenta[b]naphthalen-5-yl benzoate was obtained. The product was then dissolved in tetrahydrofuran (4.2 ml), and treated with acetic acid (12.6 ml) and distilled water (4.2 ml) overnight at room temperature. The reaction then was diluted with saturated sodium bicarbonate aqueous (50 ml) and extracted with ethyl acetate (60 ml). The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. The product was obtained in a crystalline form. MP: 140~141° C. Yield: 68%.

The product was further analyzed by HPLC to confirm that no para-cyclized isomer was found in the crystalline product.

$^1$H-NMR (CDCl$_3$): δ 8.19 (d, 2H), 7.63 (t, 1H), 7.50 (t, 2H), 7.18 (t, 1H), 7.03 (d, 1H), 6.99 (d, 1H), 5.50~5.40 (m, 2H), 4.04~4.00 (m, 1H), 3.66~3.62 (m, 1H), 3.04 (br s, 1H), 2.88 (br s, 1H), 2.68 (dd, 1H), 2.56 (dd, 1H), 2.44 (dd, 1H), 2.38 (dd, 1H), 2.32~2.28 (m, 1H), 2.14—2.00 (m, 2H), 1.76~1.71 (m, 1H), 1.58~1.53 (m, 1H), 1.48~1.32 (m, 7H), 1.08 (q, 1H), 0.90 (t, 3H)

13C-NMR (CDCl₃) δ 165.31, 148.44, 140.86, 136.22, 133.60, 133.21, 130.83, 130.19, 129.38, 128.60, 126.49, 125.80, 119.70, 75.69, 73.06, 53.73, 40.14, 37.10, 32.29, 32.11, 31.72, 27.12, 25.18, 22.62, 14.01

Example 25

(1R,2R,3aS,9aS)-2,3,3a,4,9,9a-hexahydro-2-hydroxy-1-((S)-3-hydroxyoctyl)-1H-cyclopenta[b]naphthalen-5-yl benzoate

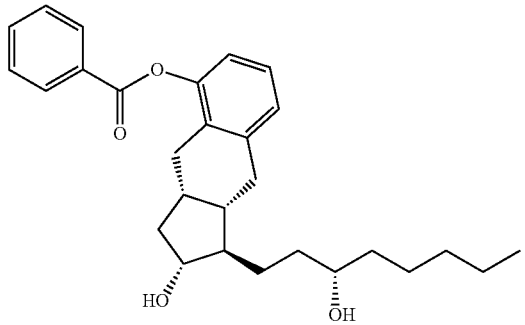 [SMILES: CCCCC[C@H](O)CC[C@@H]1[C@H]2Cc3cccc(OC(=O)c4ccccc4)c3C[C@H]2C[C@H]1O]

(1R,2R,3aS,9aS)-2,3,3a,4,9,9a-hexahydro-2-hydroxy-1-((S,E)-3-hydroxyoct-1-enyl)-1H-cyclopenta[b]naphthalen-5-yl benzoate (0.35 g, 0.8 mmol) in dry methanol (2.5 ml) was treated with 5% Pd/C (0.05 g, 20% wt) and stirred under hydrogen for 5 hours at room temperature. Then, the reaction mixture was filtered with celite pad. The solvent was evaporated off under vacuum. The crude product was purified by chromatography on silica gel using a mixture of hexane and ethyl acetate as a gradient eluent. Yield: 87%.

¹H-NMR (CDCl₃): δ 8.20 (d, 2H), 7.62 (t, 1H), 7.50 (t, 2H), 7.18 (t, 1H), 7.05 (d, 1H), 6.90 (d, 1H), 3.73~3.66 (m, 1H), 3.61~3.59 (m, 1H), 2.80 (dd, 1H), 2.64 (dd, 1H), 2.51 (dd, 1H), 2.34 (dd, 1H), 2.23~2.18 (m, 1H), 2.13~2.03 (m, 1H), 1.92~1.86 (m, 2H), 1.66~1.63 (m, 2H), 1.56~1.52 (m, 2H), 1.46—1.41 (m, 3H), 1.32~1.16 (m, 7H), 1.14~1.11 (m, 1H), 0.88 (t, 3H)

13C-NMR (CDCl₃): δ 165.16, 148.30, 141.09, 133.52, 131.03, 130.18, 129.51, 128.58, 126.39, 125.56, 119.60, 75.52, 52.32, 41.25, 37.44, 34.94, 33.72, 32.59, 31.89, 28.56, 27.38, 25.34, 22.61, 14.00

Example 26

Methyl 2-((1R,2R,3aS,9aS)-2,3,3a,4,9,9a-hexahydro-2-hydroxy-1-((S,E)-3-hydroxyoct-1-enyl)-1H-cyclopenta[b]naphthalen-5-yloxy)acetate

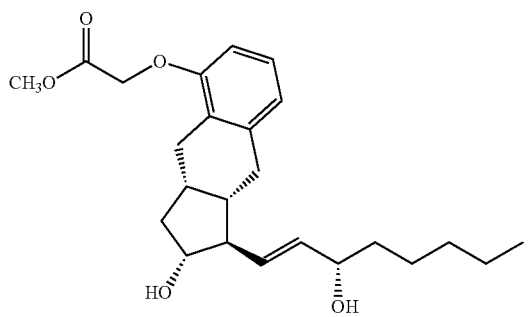

(1R,2R,3aS,9aS)-2,3,3a,4,9,9a-hexahydro-2-(tert-butyldimethylsilyoxy)-1-((S,E)-3-(tert-butyldimethylsilyoxy)oct-1-enyl)-1H-cyclopenta[b]naphthalen-5-ol (0.5 g, 0.89 mmol) in methyl bromoacetate (3 ml) was treated with 50% NaOH (1 g). The mixture was stirred at room temperature for 60 min. The reaction mixture was cooled to 10° C. and 3N HCl was added slowly until pH=7, and then the reaction was exacted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. 0.2 g of Methyl 2-((1R,2R,3aS,9aS)-2,3,3a,4,9,9a-hexahydro-2-(tert-butyldimethylsilyoxy)-1-((S,E)-3-hydroxyoct-1-enyl)-1H-cyclopenta[b]naphthalen-5-yloxy)acetate was obtained. The product was then dissolved in THF (1.3 ml), acetic acid (3.9 ml) and distilled water (1.3 ml) for overnight at room temperature. The reaction mixture was poured to saturated sodium bicarbonate aqueous (1.0 ml) and stirred for 30 minutes. The reaction mixture was phase separated and the aqueous layer was extracted with 20 ml ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. The titled compound was obtained in a crystalline form. (Yield: 58%)

Examples 27~30

(1R,2R,3aS,9aS)-2,3,3a,4,9,9a-hexahydro-1-((S)-3-hydroxyoctyl)-1H-cyclopenta[b]naphthalene-2,5-diol

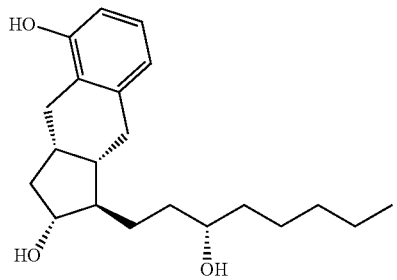 [SMILES: CCCCC[C@H](O)CC[C@@H]1[C@H]2Cc3cccc(O)c3C[C@H]2C[C@H]1O]

Example 27

The same procedure as described in Example 22 was repeated except that the equimolar of the substrate used in the reaction was (1R,2R,3aS,9aS)-2,3,3a,4,9,9a-hexahydro-2-(tert-butyldimethylsilyoxy)-1-((S)-3-(tert-butyldimethylsilyoxy)octyl)-1H-cyclopenta[b]naphthalen-5-ol (from example 20) instead of (1R,2R,3aS,9aS)-2,3,3a,4,9,9a-hexahydro-2-(tert-butyldimethylsilyoxy)-1-((S,E)-3-(tert-butyldimethylsilyoxy)oct-1-enyl)-1H-cyclopenta[b]naphthalen-5-ol. The titled compound was prepared and obtained in a crystalline form. (Yield: 83%).

Example 28

(1R,2R,3aS,9aS)-2,3,3a,4,9,9a-hexahydro-1-((S,E)-3-hydroxyoct-1-enyl)-1H-cyclopenta[b]naphthalene-2,5-diol (2.5 g, 0.008 mol, from Example 21 or 22) in dry methanol (25 ml) was treated with potassium hydroxide (0.5 g, 0.008 mol), then with 5% Pd/C (0.5 g, 20% wt) under hydrogen for overnight at room temperature. Then, the reaction mixture was filtered with celite pad. The solvent was evaporated off under vacuum. The crude product was purified by chromatography on silica gel using a mixture of hexane and ethyl acetate as a gradient eluent. The titled compound was obtained in a crystalline form. Yield: 72%

Example 29

(1R,2R,3aS,9aS)-2,3,3a,4,9,9a-hexahydro-2-hydroxy-1-((S)-3-hydroxyoctyl)-1H-cyclopenta[b]naphthalen-5-yl benzoate (0.2 g, 0.008 mol, from Example 25) was treated with 1 mL of sodium hydroxide (5% in methanol), then stirred at room temperature for 60 mins. The reaction mixture was diluted with 3N HCl (1 ml) and ethyl acetate (10 mL). The reaction mixture was phase separated and the aqueous layer was extracted with ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. The titled compound was obtained in a crystalline form. Yield: 85%.

Example 30

(1R,2R,3aS,9aS)-2,3,3a,4,9,9a-hexahydro-2-hydroxy-1-((S,E)-3-hydroxyoct-1-enyl)-1H-cyclopenta[b]naphthalen-5-yl benzoate (0.25 g, 0.6 mmol, from Example 24) in dry methanol (2 ml) was treated with 5% Pd/C (0.05 g, 20% wt) and stirred under hydrogen for 28 hours at room temperature. Then, the reaction mixture was filtered with celite pad. The solvent was evaporated off under vacuum. The crude product was purified by chromatography on silica gel using a mixture of hexane and ethyl acetate as a gradient eluent. The titled compound was obtained in a crystalline form. Yield: 73%

$^1$H-NMR (CD$_3$OD): δ 6.98 (t, 1H), 6.62 (d, 2H), 3.63~3.56 (m, 1H), 3.52~3.51 (m, 1H), 2.71~2.56 (m, 3H), 2.49~2.42 (m, 1H), 2.36~2.29 (m, 1H), 2.07~2.03 (m, 1H), 1.95~1.83 (m, 1H), 1.76~1.50 (m, 3H), 1.48~1.21 (m, 9H), 1.20~1.02 (m, 2H), 0.91 (t, 3H)

$^{13}$C-NMR (CD$_3$OD): δ 154.36, 140.87, 126.00, 125.03, 119.48, 112.78, 76.58, 71.92, 51.55, 41.33, 41.00, 37.29, 35.05, 33.57, 33.15, 32.16, 28.66, 25.55, 25.50, 22.70, 13.44

Examples 31 & 32

2-((1R,2R,3aS,9aS)-2,3,3a,4,9,9a-hexahydro-2-hydroxy-1 ((S,E)-3-hydroxyoct-1-enyl)-1H-cyclopenta[b]naphthalen-5-yloxy)acetonitrile

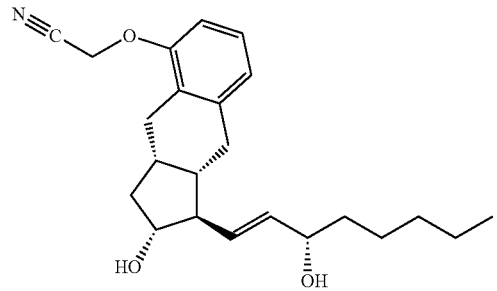 [SMILES: CCCCC[C@H](O)/C=C/[C@@H]1[C@H]2Cc3cccc(OCC#N)c3C[C@H]2C[C@H]1O]

Example 31

(1R,2R,3aS,9aS)-2,3,3a,4,9,9a-hexahydro-1-((S,E)-3-hydroxyoct-1-enyl)-1H-cyclopenta[b]naphthalene-2,5-diol (1.6 g, 0.004 mol) in dry acetone (16 ml) was treated with K$_2$CO$_3$ (1.66 g, 0.012 mol), chloroacetonitrile (0.51 ml, 0.008 mol) and tetrabutylammonium bromide (0.32 g, 0.001 mmol). The mixture was heated at 30° C. overnight. Then, the reaction mixture was filtered with celite pad. The filtrate was evaporated off under vacuum. The crude product was purified by chromatography on silica gel using a mixture of hexane and ethyl acetate as a gradient eluent. The titled compound was obtained in a crystalline form. Yield: 89%

Example 32

(1R,2R,3aS,9aS)-2,3,3a,4,9,9a-hexahydro-2 (tert-butyldimethylsilyoxy)-1-(S,E)-3-(tert-butyldimethylsilyoxy) oct-1-enyl)-1H-cyclopenta[b]naphthalen-5-ol (6.4 g, 0.011 mmol) in dry acetone (64 ml) was treated with K$_2$CO$_3$ (6.64 g, 0.048 mol), chloroacetonitrile (2 ml, 0.032 mol) and tetrabutylammonium bromide (1.28 g, 0.004 mmol). The mixture was heated at 30° C. overnight. Then, The reaction mixture was filtered with celite pad. The filtrate was evaporated off under vacuum. The crude protected benzindene nitrile[2-((1R,2R,3aS,9aS)-2,3,3a,4,9,9a-hexahydro-2-(tert-butyldimethylsilyoxy)-1 (S,E)-3-(tert-butyldimethylsilyoxy) oct-1-enyl)-1H-cyclopenta[b]naphthalen-5-yloxy) acetonitrile] was obtained. The crude protected benzindene nitrile was then dissolved in THF (19.2 ml), then acetic acid (57.6 ml) and distilled water (19.2 ml) overnight at room temperature. The reaction mixture was poured to saturated sodium bicarbonate aqueous (200 ml) and stirred for 30 minutes. The reaction mixture was phase separated and the aqueous layer was extracted with 300 ml ethyl acetate. The organic layers were combined and dried over anhydrous magnesium sulfate. The solid was filtered off. The solvent was evaporated off under vacuum. The crude product was purified by chromatography on silica gel using a mixture of hexane and ethyl acetate as a gradient eluent. Yield of the titled compound was 3.43 g containing a trace amount of para-cyclized isomer. The para-cyclized isomer was removed by crystallization from isopropyl ether/heptane. 2.74 g titled compound was obtained in a crystalline form (white to off-white powder). MP: 58° C. (Yield: 67%)

$^1$H-NMR (CDCl$_3$): δ 7.15 (t, 1H), 6.87 (d, 1H), 6.83 (d, 1H), 5.53~5.46 (m, 2H), 4.76 (s, 2H), 4.09~4.01 (m, 1H), 3.76~3.70 (m, 1H), 2.68—2.59 (m, 2H), 2.43~2.32 (m, 2H), 2.24~2.18 (m, 1H), 2.07~2.03 (m, 1H), 1.58~1.55 (m, 1H), 1.51~1.48 (m, 1H), 1.40~1.31 (m, 8H), 1.07 (q, 1H), 0.91 (t, 3H)

$^{13}$C-NMR (CDCl$_3$): δ 153.85, 141.16, 136.18, 132.71, 128.08, 126.58, 123.24, 115.41, 110.49, 75.60, 73.06, 56.72, 54.44, 40.30, 37.21, 32.40, 31.99, 31.69, 25.60, 25.21, 22.62, 14.02

Example 33

2-((1R,2R,3aS,9aS)-2,3,3a,4,9,9a-hexahydro-2-hydroxy-1-((S)-3-hydroxyoctyl)-1H-cyclopenta[b]naphthalen-5-yloxy)acetonitrile

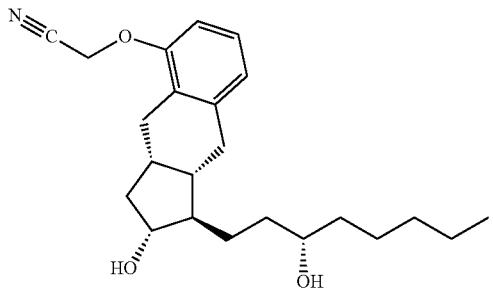 [SMILES: CCCCC[C@H](O)CC[C@@H]1[C@H]2Cc3cccc(OCC#N)c3C[C@H]2C[C@H]1O]

(1R,2R,3aS,9aS)-2,3,3a,4,9,9a-hexahydro-1-((S)-3-hydroxyoctyl)-1H-cyclopenta[b]naphthalene-2,5-diol (2 g, 0.005 mol) in dry acetone (20 ml) was treated with K$_2$CO$_3$ (2.07 g, 0.015 mol), chloroacetonitrile (0.64 ml, 0.010 mol) and tetrabutylbromide (0.32 g, 0.001 mmol). The mixture was heated at 30° C. overnight. Then, the reaction mixture was filtered with celite pad. The filtrate was evaporated off under vacuum. The crude product was purified by chromatography on silica gel using a mixture of hexane and ethyl acetate as a gradient eluent. Yield: 82%

Examples 34 & 35

2-((1R,2R,3aS,9aS)-2,3,3a,4,9,9a-hexahydro-2-hydroxy-1-((S,E)-3-hydroxyoct-1-enyl)-1H-cyclopenta[b]naphthalen-5-yloxy)acetic acid

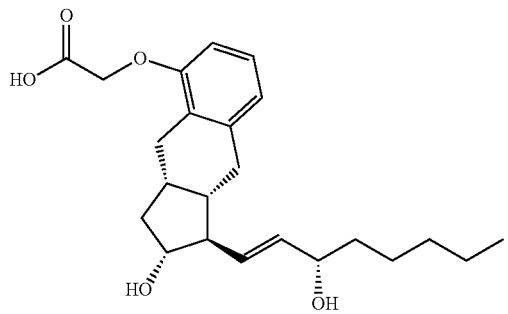 [SMILES: CCCCC[C@H](O)/C=C/[C@@H]1[C@H]2Cc3cccc(OCC(=O)O)c3C[C@H]2C[C@H]1O]

Example 34

2-((1R,2R,3aS,9aS)-2,3,3a,4,9,9a-hexahydro-2-hydroxy-1-((S,E)-3-hydroxyoct-1-enyl)-1H-cyclopenta[b]naphthalen-5-yloxy)acetonitrile (1.6 g, 0.004 mol) in isopropyl alcohol (16 ml) was treated with 20% KOH (5 ml) and refluxed for 3 hr then cooled to 10° C. and 3N HCl was added slowly until pH=~8. The solvent was removed in vacuo. Ethyl acetate and brine were added and then 3N HCl was added slowly until pH=2. The reaction mixture was extracted with ethyl acetate. The combined ethyl acetate extracts were dried over anhydrous magnesium sulfate. The solid was filtered off. The solvent was evaporated off under vacuum. The crude product was purified by crystallization from ethanol/H$_2$O. 1.2 g titled compound was obtained in a crystalline form.

Example 35

The procedure as described in Example 29 was repeated except that the equimolar of the substrate used in the reaction was methyl 2-(1R,2R,3aS,9aS)-2,3,3a,4,9,9a-hexahydro-2-hydroxy-1-((S,E)-3-hydroxyoct-1-enyl)-1H-cyclopenta[b]naphthalen-5-yloxy)acetate. The titled compound was prepared and obtained in a crystalline form. Yield: 82%.

$^1$H-NMR (CD$_3$OD): δ 7.06 (t, 1H), 6.74 (d, 1H), 6.71 (d, 1H), 5.53 (dd, 1H), 5.44 (dd, 1H), 4.62 (s, 2H), 4.01 (q, 1H), 3.72~3.66 (m, 1H), 2.77 (dd, 1H), 2.62 (dd, 2H), 2.44 (dd, 1H), 2.41~2.35 (m, 1H), 2.16~2.02 (m, 2H), 1.67 (q, 1H), 1.59~1.34 (m, 8H), 1.06 (q, 1H), 0.93 (t, 3H)

$^{13}$C-NMR (CD$_3$OD): δ 172.94, 156.75, 141.80, 136.45, 134.11, 128.48, 127.32, 122.58, 110.88, 76.66, 73.94, 66.54, 57.22, 41.79, 41.64, 38.31, 33.74, 32.94, 32.81, 26.41, 26.34, 23.75, 14.41

Examples 36 & 37

Preparation of Treprostinil 2-((1R,2R,3aS,9aS)-2,3,3a,4,9,9a-hexahydro-2-hydroxy-1-((S)-3-hydroxyoctyl)-H-cyclopenta[b]naphthalen-5-yloxy)acetic acid

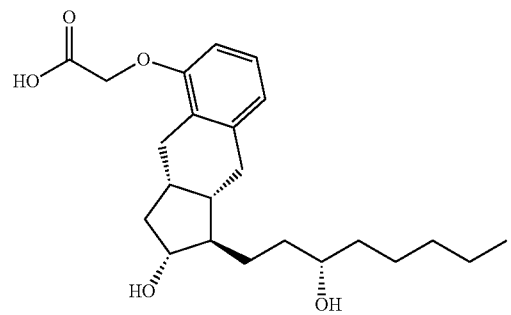 [SMILES: CCCCC[C@H](O)CC[C@@H]1[C@H]2Cc3cccc(OCC(=O)O)c3C[C@H]2C[C@H]1O]

Example 36

Preparation of Treprostinil from the Product of Example 33

2-((1R,2R,3aS,9aS)-2,3,3a,4,9,9a-hexahydro-2-hydroxy-1-((S)-3-hydroxyoctyl)-1H-cyclopenta[b]naphthalen-5-yloxy)acetonitrile (2 g, 0.05 mol) in methanol (18 ml) was treated with 20% KOH (6 ml) and refluxed for 3 hr. The reaction was then cooled to 10° C. and 3N HCl was added slowly until pH=~8. The solvent was removed in vacuo. Ethyl acetate and brine were added and then 3N HCl was added slowly until pH=2. The reaction mixture was extracted with ethyl acetate. The combined ethyl acetate extracts were dried over anhydrous magnesium sulfate. The solid was filtered off. The solvent was evaporated off under vacuum. The crude product was purified by crystallization from ethanol/H$_2$O. The titled compound was obtained in a crystalline form. Yield: 81%.

Example 37

Preparation of Treprostinil from the Product of Examples 34 & 35

2-((1R,2R,3aS,9aS)-2,3,3a,4,9,9a-hexahydro-2-hydroxy-1-((S,E)-3-hydroxyoct-1-enyl)-1H-cyclopenta[b]naphthalen-5-yloxy)acetic acid (2.5 g, 0.008 mol) in dry methanol (25 ml) was treated with potassium hydroxide (0.5 g, 0.008 mol), then with 5% Pd/C (0.5 g, 20% wt) under hydrogen overnight at room temperature. Then, the reaction mixture was filtered with celite pad. The solvent was evaporated off under vacuum. The residues was diluted with 50 nm ethyl, acetate and 50 ml saturated sodium bicarbonate aqueous. The mixture was phase separated and the organic layers was extracted with 50 ml saturated sodium bicarbonate aqueous. The aqueous layers were combined and then 3N HCl was added slowly until pH=~2. The aqueous layer was extracted with 100 ml ethyl acetate. The organic layers were combined and dried over anhydrous magnesium sulfate. The solid was filtered off. The solvent was evaporated off under vacuum. The crude product was purified by crystallization. The titled compound was obtained in a crystalline form. Yield: 88%

$^1$H-NMR (CDCl$_3$): δ 7.08 (t, 1H), 6.83 (d, 1H), 6.69 (d, 1H), 4.65 (s, 2H), 3.75 (q, 1H), 3.67~3.58 (m, 1H), 2.82~2.73 (m, 2H), 2.62—2.58 (m, 1H), 2.51~2.47 (m, 1H), 2.29~2.27 (m, 1H), 2.20—2.15 (m, 1H), 1.91~1.84 (m, 1H), 1.66~1.65 (m, 1H), 1.49~1.33 (m, 4H), 1.32~1.21 (m, 8H), 1.17 (q, 1H), 0.91 (t, 3H)

$^{13}$C-NMR (CDCl$_3$): δ170.86, 154.80, 141.12, 127.92, 126.32, 122.18, 110.25, 76.75, 72, 75, 65.96, 52.28, 41.51, 41.39, 37.47, 35.02, 33.60, 32.98, 31.94, 28.69, 26.06, 25.35, 22.61, 13.94

We claim:

1. A process for preparing the compound of Formula 8d

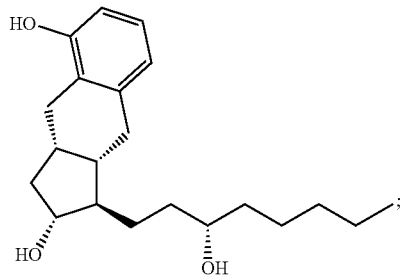

8d comprising the steps of:
(1) esterifying the compound of Formula 6d

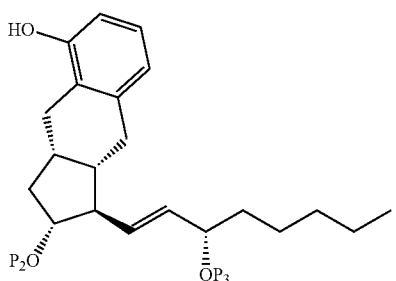

6d wherein P$_2$ and P$_3$ are protecting groups for the hydroxyl groups, to form an ester compound of Formula 10d

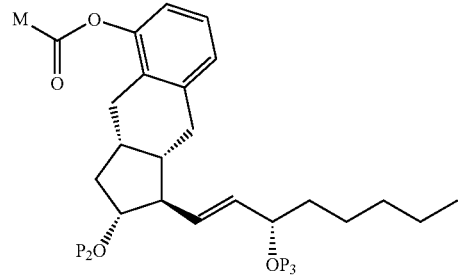

10d wherein M is a lower alkyl, or an unsubstituted or substituted phenyl;

(2) removing the P$_2$ and P$_3$ groups to form a compound of Formula 11d

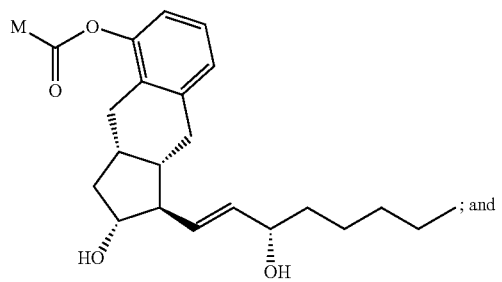

11d

; and (3) hydrogenating the double bond in the ω-side chain of the compound of Formula 11d and then deacylating the hydrogenated compound; or deacylating the compound of Formula 11d and then hydrogenating the double bond in the ω-side chain of the deacylated compound to form a compound of Formula 8d.

2. The process according to claim 1, wherein M is phenyl or 4-phenylphenyl.

3. A compound of Formula 1e

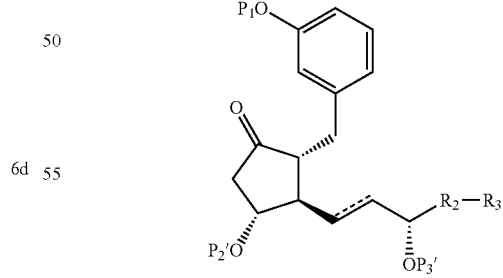

1e wherein P$_1$ is an unsubstituted or substituted benzyl; ══ is single bond or double bond; R$_2$ is a single bond or a C$_{1-4}$-alkylene or —CH$_2$O—; R$_3$ is a C$_{1-7}$-alkyl or an aryl or an aralkyl group, each of which is unsubstituted or substituted by a C$_{1-4}$-alkyl, a halogen, or a trihalomethyl; P$_2$' and P$_3$' are respectively P$_2$ and P$_3$ as defined in claim 1 as protecting groups for the hydroxy group or are independently H.

4. A compound of Formula 8D-1
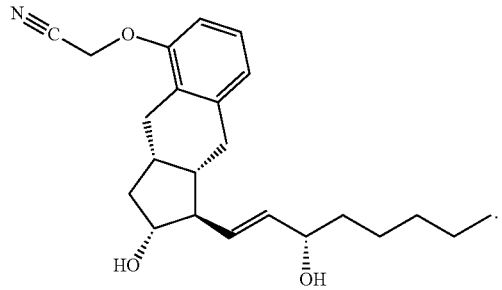
5. A compound of Formula 11-1
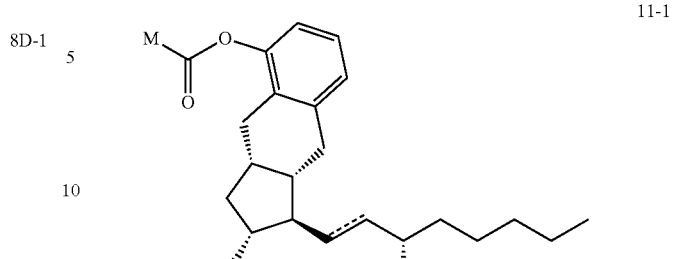
wherein M is methyl, phenyl or 4-phenylphenyl; and ══ is a single or double bond.
* * * * *